United States Patent
Ito et al.

(10) Patent No.: US 11,208,108 B2
(45) Date of Patent: Dec. 28, 2021

(54) MONITORING BIOLOGICAL INFORMATION OF A PASSENGER IN A VEHICLE

(71) Applicant: TOYOTA JIDOSHA KABUSHIKI KAISHA, Toyota (JP)

(72) Inventors: Masaki Ito, Toyota (JP); Masashi Mori, Nagoya (JP); Miyuki Kubota, Gotenba (JP); Chiharu Aoki, Numazu (JP); Nanami Sano, Susono (JP); Daichi Sakakibara, Susono (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/936,890

(22) Filed: Jul. 23, 2020

(65) Prior Publication Data

US 2021/0039652 A1 Feb. 11, 2021

(30) Foreign Application Priority Data

Aug. 9, 2019 (JP) .............................. JP2019-147967

(51) Int. Cl.
```
B60W 40/08      (2012.01)
A61B 5/0205     (2006.01)
A61B 5/00       (2006.01)
H04W 4/40       (2018.01)
H04W 4/90       (2018.01)
H04W 4/029      (2018.01)
```
(52) U.S. Cl.
CPC ......... *B60W 40/08* (2013.01); *A61B 5/02055* (2013.01); *A61B 5/6802* (2013.01); *A61B 5/742* (2013.01); *H04W 4/029* (2018.02); *H04W 4/40* (2018.02); *H04W 4/90* (2018.02); *B60W 2540/01* (2020.02); *B60W 2540/221* (2020.02); *B60W 2540/26* (2013.01)

(58) Field of Classification Search
None
See application file for complete search history.

(56) References Cited

U.S. PATENT DOCUMENTS

2012/0197138 A1* 8/2012 Vrazic ................. A61B 5/1102
                                                   600/484
2015/0342542 A1* 12/2015 An ....................... G08B 25/016
                                                   455/404.2

(Continued)

FOREIGN PATENT DOCUMENTS

| JP | 2016-018474 A | 2/2016 |
| JP | 2017-091013 A | 5/2017 |
| JP | 2018-195250 A | 12/2018 |

*Primary Examiner* — Adolf Dsouza
(74) *Attorney, Agent, or Firm* — Oliff PLC

(57) ABSTRACT

An information providing system for a vehicle includes: first and second mobile terminals worn by a driver and fellow passenger, respectively of the vehicle, and an information providing device, which are communicated with each other. Further, the information providing device includes a control unit that executes information provision control for generating information indicating that the physical condition of the fellow passenger is the predetermined state and transmitting the generated information to the first mobile terminal, in a case where it is determined that the physical condition of the fellow passenger is the predetermined state.

12 Claims, 9 Drawing Sheets

(56) References Cited

U.S. PATENT DOCUMENTS

| | | | | |
|---|---|---|---|---|
| 2016/0001781 | A1* | 1/2016 | Fung | B60K 28/02 |
| | | | | 701/36 |
| 2017/0231544 | A1* | 8/2017 | Satoi | A61B 5/7275 |
| | | | | 600/479 |
| 2017/0242428 | A1* | 8/2017 | Pal | A61B 5/021 |
| 2019/0304309 | A1* | 10/2019 | Sakamoto | B60W 50/14 |
| 2020/0074491 | A1* | 3/2020 | Scholl | G06F 11/3423 |

\* cited by examiner

MONITORING BIOLOGICAL INFORMATION OF A PASSENGER IN A VEHICLE

CROSS-REFERENCE TO RELATED APPLICATION(S)

The present application claims priority to and incorporates by reference the entire contents of Japanese Patent Application No. 2019-147967 filed in Japan on Aug. 9, 2019.

BACKGROUND

The present disclosure relates to an information providing system for a vehicle, an information providing method for a vehicle, an information providing device, and a recording medium.

Japanese Laid-open Patent Publication No. 2016-018474 discloses a vehicle control system which includes a wearable terminal worn on a body of a driver to measure biological information of the driver and an in-vehicle device mounted in a vehicle to control the vehicle and in which communication is performed between the wearable terminal and the in-vehicle device while the vehicle is traveling. In such a vehicle control system, when the in-vehicle device receives the biological information of the driver transmitted from the wearable terminal, the in-vehicle device determines whether the driver is in a state where he/she cannot drive the vehicle on the basis of the biological information, and performs control to automatically stop the vehicle that is traveling in a case where it is determined that the driver is in the state where he/she cannot drive the vehicle.

SUMMARY

There is a need for providing an information providing system for a vehicle, an information providing method for a vehicle, an information providing device, and a recording medium capable of providing information regarding a physical condition of a fellow passenger to a driver while the vehicle is traveling, using a mobile terminal that can be worn by an occupant of the vehicle.

According to an embodiment, an information providing system for a vehicle, includes: a first mobile terminal that is worn by a driver of the vehicle; a second mobile terminal that is worn by a fellow passenger of the vehicle; and an information providing device that transmits and receives information to and from the first mobile terminal and the second mobile terminal. Further, the first mobile terminal includes: a first communication unit that transmits and receives information to and from the information providing device; and a display unit that displays the information received by the first communication unit within a field of view of the driver in a state where the first mobile terminal is worn by the driver, the second mobile terminal includes: a measurement unit that measures biological information of the fellow passenger in a state where the second mobile terminal is worn by the fellow passenger while the vehicle is traveling; and a second communication unit that transmits the biological information measured by the measurement unit to the information providing device, and the information providing device includes: a third communication unit that receives the biological information transmitted from the second mobile terminal and transmits information to the first mobile terminal, while the vehicle is traveling; a determination unit that determines whether a physical condition of the fellow passenger is a predetermined state on the basis of the biological information received by the third communication unit; and a control unit that executes information provision control for generating information indicating that the physical condition of the fellow passenger is the predetermined state and transmitting the generated information to the first mobile terminal, in a case where it is determined by the determination unit that the physical condition of the fellow passenger is the predetermined state.

According to an embodiment, an information providing method for a vehicle executed by an information providing system for a vehicle, the information providing system for a vehicle including a first mobile terminal that is worn by a driver of the vehicle, a second mobile terminal that is worn by a fellow passenger of the vehicle, and an information providing device that transmits and receives information to and from the first mobile terminal and the second mobile terminal, includes: a measuring step of measuring biological information of the fellow passenger by the second mobile terminal worn by the fellow passenger while the vehicle is traveling; a first transmitting step of transmitting the measured biological information to the information providing device by the second mobile terminal; a first receiving step of receiving the biological information transmitted from the second mobile terminal by the information providing device while the vehicle is traveling; a determining step of determining whether a physical condition of the fellow passenger is a predetermined state on the basis of the received biological information, by the information providing device; a generating step of generating information indicating that the physical condition of the fellow passenger is the predetermined state by the information providing device in a case where the physical condition of the fellow passenger is determined to be the predetermined state; an information providing step of transmitting the generated information from the information providing device to the first mobile terminal; a second receiving step of receiving the information provided from the information providing device by the first mobile terminal; and a displaying step of displaying the information received by the second receiving step within a field of view of the driver by the first mobile terminal worn by the driver.

According to an embodiment, an information providing device that transmits and receives information from and to a first mobile terminal worn a driver of a vehicle and a second mobile terminal worn by a fellow passenger of the vehicle, includes: a communication unit that receives biological information of the fellow passenger measured and transmitted by the second mobile terminal worn by the fellow passenger while the vehicle is traveling; a determination unit that determines whether a physical condition of the fellow passenger is a predetermined state on the basis of the received biological information; and a control unit that executes information provision control for generating information indicating that the physical condition of the fellow passenger is the predetermined state and transmitting the generated information to the first mobile terminal, in a case where it is determined that the physical condition of the fellow passenger is the predetermined state.

According to an embodiment, a non-transitory computer readable recording medium storing a program therein, the program causing a computer that transmits and receives information from and to a first mobile terminal and a second mobile terminal to function as an information providing device, the first mobile terminal being worn by a driver of the vehicle and the second mobile terminal being worn by a fellow passenger of the vehicle. Further, the program causes the computer to execute: a receiving step of receiving biological information of the fellow passenger measured and transmitted by the second mobile terminal worn by the fellow passenger while the vehicle is traveling; a determining step of determining whether a physical condition of the fellow passenger is a predetermined state on the basis of the received biological information; and an information providing step of generating information indicating that the physical condition of the fellow passenger is the predetermined state and transmitting the generated information to the first mobile terminal, in a case where it is determined that the physical condition of the fellow passenger is the predetermined state.

DETAILED DESCRIPTION

In the related art, in addition to a driver, an occupant (fellow passenger) may be in the same vehicle. In this case, if a poor physical condition of the fellow passenger occurs while the vehicle is traveling, the driver drives the vehicle while paying attention to a physical condition of the fellow passenger. In such a case, with a configuration described in Japanese Laid-open Patent Publication No. 2016-018474, the driver could not recognize the physical condition of the fellow passenger over the wearable terminal.

Hereinafter, an information providing system for a vehicle according to an embodiment of the present disclosure will be specifically described with reference to the accompanied drawings. Note that the present disclosure is not limited to embodiments described below.

Figure 1:
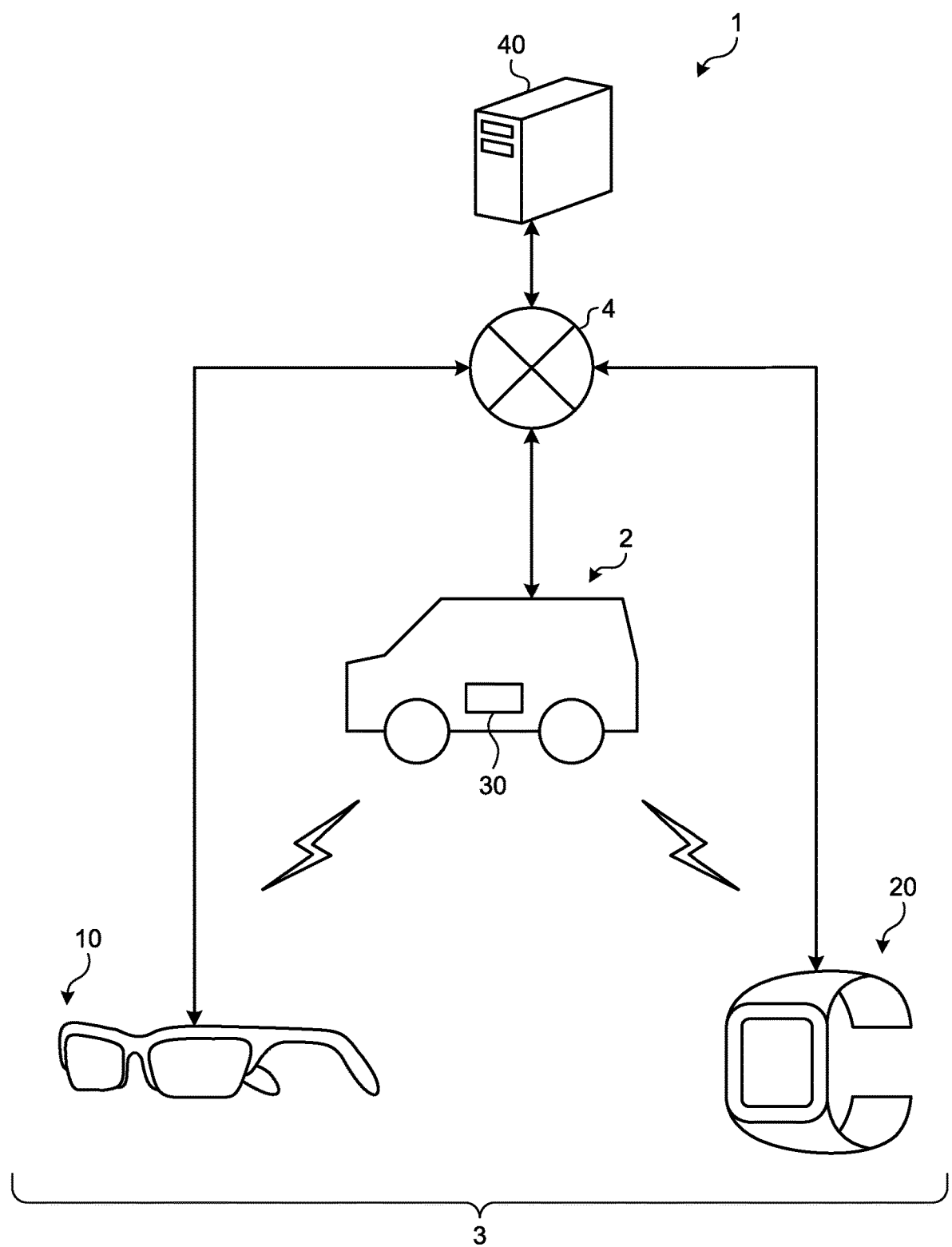
FIG. 1 is a view schematically illustrating an entire configuration of an information providing system for a vehicle according to an embodiment.
Figure 2:
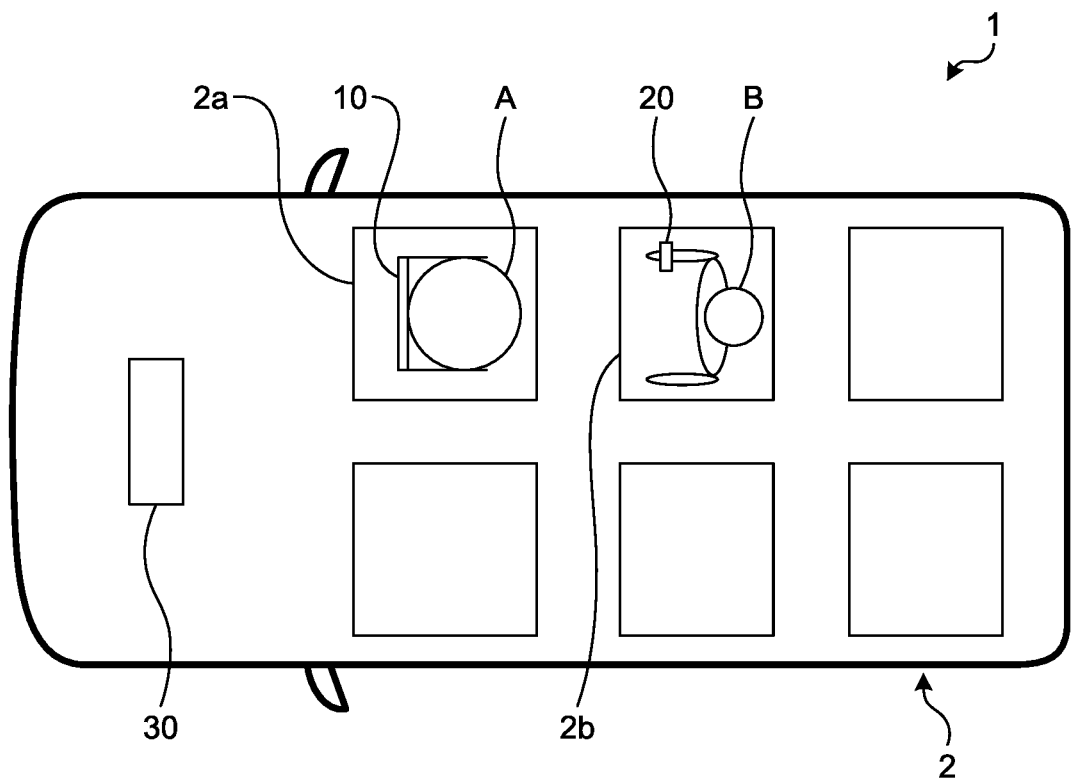
FIG. 2 is a schematic view illustrating an example of a case where a plurality of occupants are in a vehicle.

FIG. 1 is a view schematically illustrating an entire configuration of an information providing system for a vehicle according to an embodiment. FIG. 2 is a schematic view illustrating an example of a case where a plurality of occupants are in a vehicle.

An information providing system 1 for a vehicle is a system that provides information regarding a physical condition of a fellow passenger B to a driver A while a vehicle 2 is traveling, using a wearable terminal 3 that can be worn by an occupant of the vehicle 2. The wearable terminal 3 includes a first wearable terminal 10 that can be worn by the driver A of the vehicle 2 and a second wearable terminal 20 that can be worn by the fellow passenger B of the vehicle 2. The information providing system 1 for a vehicle includes the first wearable terminal 10, the second wearable terminal 20, an in-vehicle device 30, and a server 40. In this embodiment, an information providing device providing information to the first wearable terminal 10 of the driver A includes the in-vehicle device 30 and the server 40.

As illustrated in FIG. 1, the first wearable terminal 10 is a glasses-type mobile terminal that can be worn on a head of the driver A. The second wearable terminal 20 is a wristband-type mobile terminal that can be worn on a wrist of the fellow passenger B. The first wearable terminal 10 and the second wearable terminal 20 are communicably connected to the in-vehicle device 30. The in-vehicle device 30 is a device mounted in the vehicle 2, and transmits and receives information to and from the server 40 via a network 4. The server 40 is arranged outside the vehicle 2 and is communicably connected to the first wearable terminal 10, the second wearable terminal 20, and the in-vehicle device 30 via the network 4. Note that in a case where the first wearable terminal 10 and the second wearable terminal 20 are not particularly distinguished from each other, the first wearable terminal 10 and the second wearable terminal 20 may be described as a wearable terminal 3.

As illustrated in FIG. 2, the driver A sitting on a driver's seat 2a of the vehicle 2 is driving the vehicle 2 with the first wearable terminal 10 worn on his/her head. In addition, the fellow passenger B having the second wearable terminal 20 worn on his/her wrist sits on a rear seat 2b of the vehicle 2. As such, in a case where the fellow passenger B sits on the rear seat 2b of the vehicle 2, the driver A cannot directly visually recognize the fellow passenger B while driving the vehicle 2. Therefore, in the information providing system 1 for a vehicle, biological information of the fellow passenger B is measured by the second wearable terminal 20 worn by the fellow passenger B, the information regarding the physical condition of the fellow passenger B is transmitted to the first wearable terminal 10 worn by the driver A by the information providing device, and the information regarding physical condition of the fellow passenger B is displayed on a display unit 13 of the first wearable terminal 10. Note that in the following description, signs A and B for the driver and the fellow passenger will be omitted.

Figure 3:
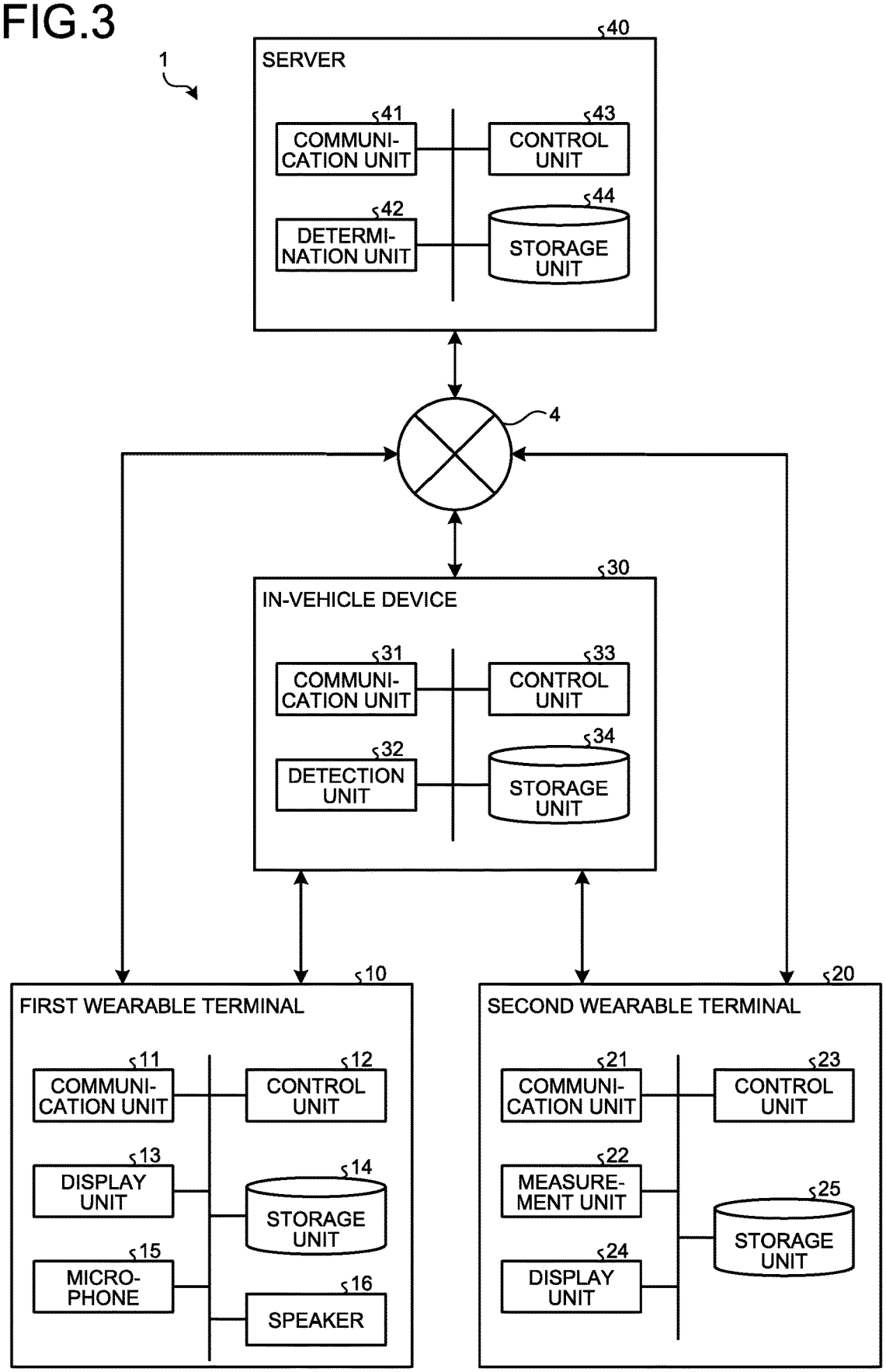
FIG. 3 is a block diagram illustrating a schematic configuration of the information providing system for a vehicle.

Here, a functional configuration of the information providing system for a vehicle will be described with reference to FIG. 3. FIG. 3 is a block diagram illustrating a schematic configuration of the information providing system for a vehicle.

The first wearable terminal 10 includes a communication unit 11, a control unit 12, a display unit 13, a storage unit 14, a microphone 15, and a speaker 16.

The communication unit 11 transmits and receives information to and from the in-vehicle device 30 and the server 40 by wireless communication. The communication unit 11 can transmit and receive information to and from the in-vehicle device 30 through short-range wireless communication, for example, Bluetooth (registered trademark). In addition, the communication unit 11 can transmit and receive information to and from the server 40 by wireless communication via the network 4, for example, wireless local area network (LAN) such as Wi-Fi (registered trademark). In addition, the communication unit 11 receives information provided from the server 40. For example, the communication unit 11 receives the information regarding the physical condition of the fellow passenger transmitted from the server 40.

The control unit 12 is an electronic control device that controls the first wearable terminal 10. The control unit 12 is configured by a general-purpose processor such as a central processing unit (CPU) having arithmetic and control functions. The control unit 12 executes communication control for controlling communication by the communication unit 11. In addition, the control unit 12 executes display control for performing image processing for generating an image to be displayed on the display unit 13 using information acquired from the in-vehicle device 30 or the server 40 by the communication unit 11 and displaying the generated image on the display unit 13.

The display unit 13 displays the image generated by the control unit 12. The display unit 13 is configured by a glasses-type see-through display, and can display the image without blocking a field of view of the driver. The driver wearing the first wearable terminal 10 can visually recognize a vehicle interior and the outside of the vehicle 2 beyond the image on the display unit 13 even in a state where the image is displayed on the display unit 13. The display unit 13 can display a predetermined image within the field of view of the driver in a state where the driver wearing the first wearable terminal 10 sits on the driver's seat 2a of the vehicle 2. The display unit 13 is included in a notification unit of the first wearable terminal 10. The notification unit is an output unit that notifies the driver of information. That is, the first wearable terminal 10 notifies the driver of the information received by the communication unit 11 by the notification unit.

In addition, the display unit 13 displays the information received by the communication unit 11. The control unit 12 performs image processing for generating an image that can be displayed on the display unit 13 according to the information received by the communication unit 11 as the display control.

The storage unit 14 is a storage device that stores image data and the like to be displayed on the display unit 13. The storage unit 14 includes a read only memory (ROM) in which various programs and the like are installed in advance, a random access memory (RAM) that stores operation parameters, data, or the like of each processing, and the like. That is, information such as various programs or terminal identification information that can identify the first wearable terminal 10 is stored in the storage unit 14 in advance. In addition, the storage unit 14 stores the information acquired by the communication unit 11 by wireless communication, in addition to the information (such as the programs) stored in advance. Then, the control unit 12 executes various controls using the programs stored in the storage unit 14 in advance. For example, the control unit 12 executes communication control for generating terminal information including the terminal identification information of the first wearable terminal 10 and transmitting the terminal information to the in-vehicle device 30 or the server 40, at the time of transmitting the information by the communication unit 11.

The microphone 15 is an input unit that receives a voice input from the driver. The control unit 12 can specify a request content from the driver on the basis of voice information input from the microphone 15. That is, the control unit 12 can execute various controls on the basis of the voice input from the microphone 15.

The speaker 16 is an output unit that outputs voice information at the time of providing voice guidance to the driver. For example, the voice information stored in the storage unit 14 is output from the speaker 16 by control of the control unit 12. The speaker 16 is included in the notification unit of the first wearable terminal 10.

The second wearable terminal 20 includes a communication unit 21, a measurement unit 22, a control unit 23, a display unit 24, and a storage unit 25.

The communication unit 21 transmits and receives information to and from the in-vehicle device 30 and the server 40 by wireless communication. The communication unit 21 can transmit and receive information to and from the in-vehicle device 30 through short-range wireless communication, for example, Bluetooth (registered trademark). In addition, the communication unit 21 can transmit and receive information to and from the server 40 by wireless communication via the network 4, for example, wireless LAN such as Wi-Fi (registered trademark). For example, the communication unit 21 transmits the biological information of the fellow passenger to the server 40.

The measurement unit 22 is a biological sensor that comes into contact with a body of the fellow passenger to measure the biological information of the fellow passenger. The measurement unit 22 can measure a pulse, a blood pressure, a respiration rate, a body temperature, a perspiration amount, a pulse width, and a sleep state as the biological information. The measurement unit 22 includes at least any one of a sensor that measures the pulse, a sensor that measures the blood pressure, a sensor that measures the respiration rate (breathing rate) or a respiration cycle, a sensor that measures the body temperature, a sensor that measures the perspiration amount, and a sensor that measures the pulse width, and a sensor that measures the sleep state. That is, the biological information to be measured by the measurement unit 22 includes at least any one of the pulse, the blood pressure, the respiration rate, the body temperature, the perspiration amount, the pulse width, and the sleep state. That is, a measured value of at least any one of the pulse, the blood pressure, the respiration rate, the body temperature, the perspiration amount, the pulse width, and the sleep state is included in the biological information measured by the measurement unit 22. For example, the sensor that measures the sleep state includes an acceleration sensor. The sleep state and an awake state can be distinguished from each other by measuring movement of the body of the fellow passenger by the acceleration sensor. Further, the measurement unit 22 measures the movement of the body and the pulse at the time of measuring the sleep state. That is, the measured value of the sleep state includes at least a measured value of the movement of the body, and may include a measured value of the pulse. Note that the measured value is synonymous with a value of a measurement item.

In addition, the measurement unit 22 can always measure the biological information of the fellow passenger in a state where the fellow passenger is in the vehicle 2. Then, the biological information (measured value) measured by the measurement unit 22 is input from the measurement unit 22 to the control unit 23.

The control unit 23 is an electronic control device that controls the second wearable terminal 20. The control unit 23 is configured by a general-purpose processor such as a CPU having arithmetic and control functions. The control unit 23 executes communication control for controlling communication by the communication unit 21. For example, the control unit 23 executes communication control for transmitting the biological information measured by the measurement unit 22 to the server 40.

In addition, the control unit 23 executes display control for performing image processing for generating an image to be displayed on the display unit 24 using the biological information measured by the measurement unit 22 and displaying the generated image on the display unit 24. Further, the control unit 23 performs storage processing of storing the biological information measured by the measurement unit 22 in the storage unit 25.

The display unit 24 displays the image generated by the control unit 23. The display unit 24 is configured by, for example, a display monitor having the same size as that of a dial of a wristwatch. The display unit 24 displays a measurement result of the biological information, time information, or the like.

The storage unit 25 is a storage device that stores the biological information and the like measured by the measurement unit 22. The storage unit 25 includes a ROM in which various programs and the like are installed in advance, a RAM that stores operation parameters, data, or the like of each processing, and the like. That is, information such as various programs or terminal identification information that can identify the second wearable terminal 20 is stored in the storage unit 25 in advance. In addition, the storage unit 25 stores the information acquired by the communication unit 21 by wireless communication, in addition to the information (such as the programs) stored in advance or information of a measurement result by the measurement unit 22. Then, the control unit 23 executes various controls such as the communication control or the display control described above using the programs stored in the storage unit 25 in advance. For example, the control unit 23 executes communication control for generating terminal information including the terminal identification information of the second wearable terminal 20 and transmitting the terminal information to the in-vehicle device 30 and the server 40, at the time of transmitting the information by the communication unit 21.

The in-vehicle device 30 includes a communication unit 31, a detection unit 32, a control unit 33, and a storage unit 34.

The communication unit 31 transmits and receives information to and from the first wearable terminal 10, the second wearable terminal 20, and the server 40. The communication unit 31 can transmit and receive information to and from the first wearable terminal 10 and the second wearable terminal 20 by short-range wireless communication, for example, Bluetooth (registered trademark). In addition, the communication unit 31 can transmit and receive information to and from the server 40 by wireless communication via the network 4, for example, wireless LAN such as Wi-Fi (registered trademark). For example, the communication unit 31 receives the terminal information including the terminal identification information from the first wearable terminal 10 and the second wearable terminal 20. Further, the communication unit 31 transmits vehicle information including identification information of the vehicle 2 and the terminal identification information of each of the first and second wearable terminals 10 and 20 to the server 40.

The detection unit 32 detects the wearable terminal 3 existing in a vehicle interior of the vehicle 2. For example, the detection unit 32 outputs a response request signal using the short-range wireless communication of the communication unit 31 for the vehicle interior of the vehicle 2. In response to the response request signal, a response signal is output from the wearable terminal 3 existing in the vehicle interior. When the communication unit 31 receives the response signal from the wearable terminal 3, the detection unit 32 detects that the wearable terminal 3 exists in the vehicle interior of the vehicle 2. That is, the detection unit 32 decides whether the wearable terminal 3 exists in the vehicle interior by determining whether the response signal according to the response request signal has been transmitted.

The control unit 33 is an electronic control device that controls the vehicle 2. The control unit 33 is configured by a general-purpose processor such as a CPU having arithmetic and control functions. The control unit 33 executes travel control of the vehicle 2, communication control for controlling communication by the communication unit 31, or the like.

For example, the control unit 33 executes short-range communication control by the communication unit 31 with each of the wearable terminals 10 and 20 detected by the detection unit 32. In the short-range communication control, the terminal information including the terminal identification information transmitted from first wearable terminal 10 and the terminal information including the terminal identification information transmitted from second wearable terminal 20 are received. The terminal identification information received by the communication unit 31 is stored in the storage unit 34.

Further, the control unit 33 executes wireless communication control by the communication unit 31 with the server 40 via the network 4. In the wireless communication control, a signal including vehicle identification information that can identify the vehicle 2, the terminal identification information of the first wearable terminal 10, and the terminal identification information of the second wearable terminal 20 is transmitted from the in-vehicle device 30 to the server 40.

In addition, signals from various sensors mounted in the vehicle 2 are input to the control unit 33. For example, a signal output from a vehicle speed sensor is input to the control unit 33. The vehicle speed sensor is a sensor that detects a vehicle speed. The control unit 33 can decide whether the vehicle 2 is being stopped or is traveling on the basis of the signal input from the vehicle speed sensor.

The storage unit 34 is a storage device that stores information regarding the vehicle 2 (vehicle information). The storage unit 34 includes a ROM in which various programs and the like are installed in advance, a RAM that stores operation parameters, data, or the like of each processing, and the like. That is, information such as various programs or vehicle identification information of the vehicle 2 is stored in the storage unit 34 in advance. In addition, the storage unit 34 stores the information acquired by the communication unit 31 by wireless communication, in addition to the information (such as the programs) stored in advance. Then, the control unit 33 executes various controls such as the travel control or the communication control of the vehicle 2 described above using the programs stored in the storage unit 34 in advance. For example, the control unit 33 executes communication control for generating an output signal including the vehicle identification information and transmitting the output signal to each of the wearable terminals 10 and 20 and the server 40, at the time of transmitting the information by the communication unit 31.

Next, the server 40 includes a communication unit 41, a determination unit 42, a control unit 43, and a storage unit 44.

The communication unit 41 transmits and receives information to and from the first wearable terminal 10, the second wearable terminal 20, and the in-vehicle device 30 via the network 4. The communication unit 41 can transmit and receive information to and from each of the wearable terminals 10 and 20 and the in-vehicle device 30 by wireless communication via the network 4, for example, wireless LAN such as Wi-Fi (registered trademark). For example, the communication unit 41 receives the biological information of the fellow passenger transmitted from the second wearable terminal 20. The biological information acquired by the communication unit 41 is the biological information of the fellow passenger measured by the second wearable terminal 20 in the vehicle interior of the vehicle 2 that is traveling. Note that as long as communication between the communication unit 41 and the network 4 is possible, it does not matter whether the communication is wireless communication or wired communication.

The determination unit 42 determines whether the physical condition of the fellow passenger is a predetermined state on the basis of the biological information acquired from the second wearable terminal 20 by the communication unit 41. The predetermined state is, for example, a state where a poor physical condition of the fellow passenger occurring.

For example, the determination unit 42 determines whether a measured value included in the biological information is out of a preset range of a predetermined normal value. A plurality of measured values may be included in the biological information. For this reason, a range of a normal value is set for each of the measured values (the pulse, the blood pressure, the respiration rate, the body temperature, the perspiration amount, the pulse width, and the sleep state) included in the biological information. As an example, in a case where a measurement item is the "pulse", the range of the normal value for the pulse is set. In addition, in a case where a measurement item is the "blood pressure", the range of the normal value for the blood pressure is set. The same applies to the other measurement items, the respiration rate, the body temperature, the perspiration amount, the pulse width, and the sleep state. Then, the determination unit 42 determines that the physical condition of the fellow passenger is abnormal, that is, a poor physical condition of the fellow passenger is occurring, in a case where at least any one of the measured values included in the biological information is out of the range of the normal value. The range of the normal value is stored in the storage unit 44 in advance. A result of physical condition determination processing by the determination unit 42 is input from the determination unit 42 to the control unit 43.

The control unit 43 is an electronic control device that controls the server 40. The control unit 43 is configured by a general-purpose processor such as a central processing unit (CPU) having arithmetic and control functions. The control unit 43 executes various controls using programs stored in the storage unit 44. For example, the control unit 43 executes communication control for controlling communication by the communication unit 41, and executes information provision control for providing information to the first wearable terminal 10 according to a determination result by the determination unit 42.

In the communication control, the vehicle identification information, the terminal identification information of the first wearable terminal 10, the terminal identification information of the second wearable terminal 20, and the biological information of the fellow passenger are received.

In the information provision control, the wearable terminals 10 and 20 worn, respectively, on the driver and the fellow passenger who are in the same vehicle 2 are specified on the basis of various information acquired by the communication unit 41. In this case, the control unit 43 can specify that the information is information regarding the same vehicle 2 by the vehicle identification information and the terminal identification information. Then, the control unit 43 associates information of the respective wearable terminals 10 and 20 with information of the vehicle 2. With respect to the information specified and associated with each other in this manner, the control unit 43 transmits fellow passenger information including information indicating that the physical condition of the fellow passenger is a predetermined state as a determination result of the physical condition determination processing by the determination unit 42 described above, to the first wearable terminal 10.

The storage unit 44 is a storage device that stores physical condition management information which is information regarding the poor physical condition. The storage unit 44 includes a ROM in which various programs and the like are installed in advance, a RAM that stores operation parameters, data, or the like of each processing, and the like. That is, information such as various programs, the information regarding the range of the normal value described above, or the physical condition management information is stored in the storage unit 44 in advance.

The physical condition management information is information including a type of poor physical condition, an occurrence factor, a symptom, and a measurement item that becomes an abnormal value. The type of poor physical condition includes "car sickness", "abdominal pain", or the like. The physical condition management information is stored in a physical condition management table having a plurality of records for each type of poor physical condition in the storage unit 44. The physical condition management table has fields of a "type of poor physical condition", an "occurrence factor", a "symptom", and a "measurement item that becomes an abnormal value". Then, the storage unit 44 stores records corresponding to a plurality of types of poor physical conditions in the physical condition management table in advance, and the control unit 43 specifies the physical condition management information from the storage unit 44 on the basis of the determination result of the physical condition determination processing by the determination unit 42.

For example, in the physical condition management table, in a record in which the "car sickness" is stored in the field of the "type of poor physical condition", an "impure air in a vehicle interior" and a "temperature or humidity at which a person feels uncomfortable" are stored in the field of the "occurrence factor", "nausea", "dizziness", and a "headache" are stored in the field of the "symptom", and a "blood pressure" and a "respiration rate" are stored in the field of the "measurement item that becomes an abnormal value". As such, in a case where a plurality of information is stored in the field of the "measurement item that becomes an abnormal value", when all the information corresponds to abnormal values, it corresponds to the type of poor physical condition. That is, in a case where only the "blood pressure" is an abnormal value, it is not specified as the "car sickness", and in a case where both of the "blood pressure" and the "respiration rate" are abnormal values, it is specified as the "car sickness".

In addition, in a case of a record in which the "abdominal pain" is stored in the field of the "type of poor physical condition", "overeating", "diarrhea", "coldness of abdomen", and "mental stress" are stored in the field of the "occurrence factor", "pain", "defecation desire", and "nausea" are stored in the field of the "symptom", and a "pulse", a "body temperature", and a "respiration rate" are stored in the field of the "measurement item that becomes an abnormal value".

Further, destination information indicating facilities or places where improvement of the physical condition is expected and information indicating a coping method of coping with the poor physical condition are stored in association with the type of poor physical condition in the storage unit 44. The physical condition management information further includes the destination information and the information indicating the coping method. That is, the physical condition management table further has fields of the "destination information" and the "coping method". In the field of the "coping method", a coping method that can be tried in the vehicle interior while the vehicle is traveling is stored. For example, in a record in which the type of poor physical condition described above is "car sickness", a "road shoulder or parking lot" is stored in the field of the "destination information" field, and "breathe slowly" and "ventilation in a vehicle" are stored in the field of the "coping method". Then, in a case where it is determined by the determination unit 42 that the poor physical condition of the fellow passenger is occurring, the control unit 43 specifies the information indicating the type of poor physical condition and specifies information indicating a coping method of coping with the poor physical condition, with reference to the physical condition management table (physical condition management information) of the storage unit 44. Then, the specified information is provided to the first wearable terminal 10 of the driver by control of the control unit 43.

In addition, the storage unit 44 stores the information acquired by the communication unit 41, in addition to the information (such as the programs) stored in advance. For example, the biological information of the fellow passenger acquired by the communication unit 41 is stored in the storage unit 44. In this case, the storage unit 44 stores the biological information of the fellow passenger from the second wearable terminal 20 in association with the vehicle information received from the in-vehicle device 30. For example, the biological information and the vehicle information are stored in a biological information table of the storage unit 44. For example, the biological information table has fields of "terminal identification information of a second wearable terminal", "biological information", an "abnormality determination flag", a "type of poor physical condition", "vehicle identification information", and "terminal identification information of a first wearable terminal". In a case where it is determined by the determination unit 42 that the poor physical condition of the fellow passenger has occurred, the control unit 43 sets a flag in the field of the "abnormality determination flag", and stores the type of poor physical condition specified by the physical condition management table in the field of the "type of poor physical condition".

Here, information provision control for providing information to the first wearable terminal 10 existing in the vehicle interior will be described with reference to FIGS. 4 and 5.

Figure 4:
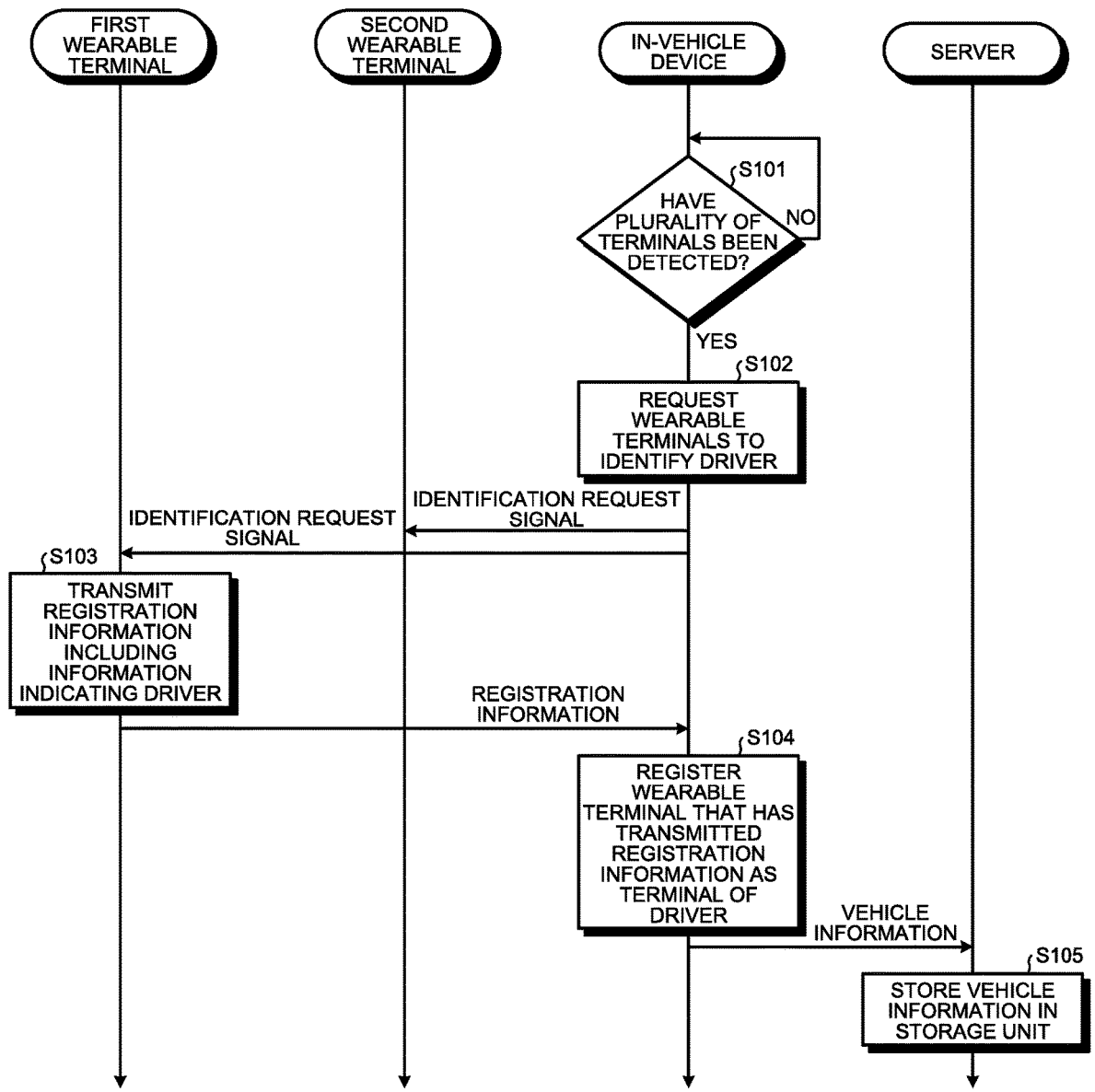
FIG. 4 is a sequence diagram illustrating control for specifying a wearable terminal of the driver.

FIG. 4 is a sequence diagram illustrating control for specifying a wearable terminal of the driver. The control illustrated in FIG. 4 is control executed by the information providing system 1 for a vehicle, and is repeatedly executed while the vehicle 2 is being stopped.

As illustrated in FIG. 4, the in-vehicle device 30 determines whether a plurality of wearable terminals 3 have been detected in the vehicle interior (Step S101). In Step S101, it is determined whether the in-vehicle device 30 has received a response signal from the wearable terminal 3 for the vehicle interior of the vehicle 2.

In a case where the plurality of wearable terminals 3 have not been detected in the vehicle interior (Step S101: No), this control routine returns to Step S101.

In a case where the plurality of wearable terminals 3 have been detected in the vehicle interior (Step S101: Yes), the in-vehicle device 30 requests the plurality of wearable terminals 3 that are detected to identify the driver (Step S102). In Step S102, a request signal (identification request signal) for identifying a terminal of the driver is transmitted to the plurality of wearable terminals 3 detected in the vehicle interior.

When the first wearable terminal 10 receives the identification request signal from the in-vehicle device 30, the first wearable terminal 10 transmits registration information indicating that the terminal is a terminal worn by the driver to the in-vehicle device 30 according to an input from the driver (Step S103). In Step S103, first, information indicating that the identification request signal has been received is displayed on the display unit 13 of the first wearable terminal 10. Thereafter, in a case where a voice input from the driver is received by the microphone 15 with respect to this display, the registration information indicating that the terminal is a terminal worn by the driver is transmitted from first wearable terminal 10 to the in-vehicle device 30. The registration information includes the terminal identification information of the first wearable terminal 10 and information that can identify that the terminal is the terminal of the driver. Note that an input method to the first wearable terminal 10 is not limited to the voice input from the driver, and may be an input method in which the driver operates an operation unit (not illustrated) of the first wearable terminal 10.

In addition, the second wearable terminal 20 also receives the identification request signal from the in-vehicle device 30. Transmission of a signal from the second wearable terminal 20 for the identification request signal is not performed. For example, although information indicating that the identification request signal has been received is displayed on the display unit 24 of the second wearable terminal 20, a signal for the identification request signal is not is generated because there is no input from the fellow passenger.

When the in-vehicle device 30 receives the registration information from the wearable terminal 3 existing in the vehicle interior, the in-vehicle device 30 registers the information assuming that the first wearable terminal 10 that has transmitted the registration information is the terminal worn by the driver (Step S104). In Step S104, the in-vehicle device 30 stores the terminal identification information included in the registration information in the storage unit 34 as information of the driver.

Further, in Step S104, the in-vehicle device 30 generates the vehicle information including the information of the wearable terminal 3 acquired by the communication unit 31 and the information of the vehicle 2 stored in the storage unit 34, and transmits the generated vehicle information to the server 40. The vehicle information includes the vehicle identification information, the terminal identification information of the first wearable terminal 10, the terminal identification information of the second wearable terminal 20, and the registration information indicating that the first wearable terminal 10 is the terminal worn by the driver.

When the server 40 receives the vehicle information from the in-vehicle device 30, the server 40 stores the vehicle information in the storage unit 44 (Step S105). In Step S105, the information included in the received vehicle information is stored in the storage unit 44 in a state where it is associated as information regarding the vehicle 2. That is, when the vehicle information is stored in the storage unit 44, the vehicle identification information, the terminal identification information of the first wearable terminal 10, the terminal identification information of the second wearable terminal 20, and the registration information included in the received vehicle information are associated with each other.

For example, the storage unit 44 of the server 40 stores a vehicle information table. The vehicle information table has fields of a "vehicle", a "wearable terminal", a "terminal of a driver", and a "terminal of a fellow passenger". In the field of the "wearable terminal", information of the plurality of wearable terminals 3 detected in the vehicle interior is stored. In the field of the "terminal of a driver", information of the first wearable terminal 10 corresponding to the registration information is stored. In the field of the "terminal of a fellow passenger", information of a terminal other than the terminal of the driver among the plurality of wearable terminals 3 detected in the vehicle interior is stored.

In Step S105, the server 40 stores the "vehicle identification information" in the field of the "vehicle", stores the "terminal identification information of the first wearable terminal" and the "terminal identification information of the second wearable terminal" in the field of the "wearable terminal", stores the "terminal identification information of the first wearable terminal" in the field of the "terminal of a driver", and the "terminal identification information of the second wearable terminal" in the field of the "terminal of a fellow passenger, with respect to the same record in the vehicle information table. Therefore, the server 40 can specify which vehicle the information received by the communication unit 41 is information regarding, with reference to the vehicle information table stored in the storage unit 44. Since information is transmitted from a plurality of vehicles other than the vehicle 2 described above to the server 40, the server 40 needs to determine which vehicle the information received by the communication unit 41 is information regarding.

Figure 5:
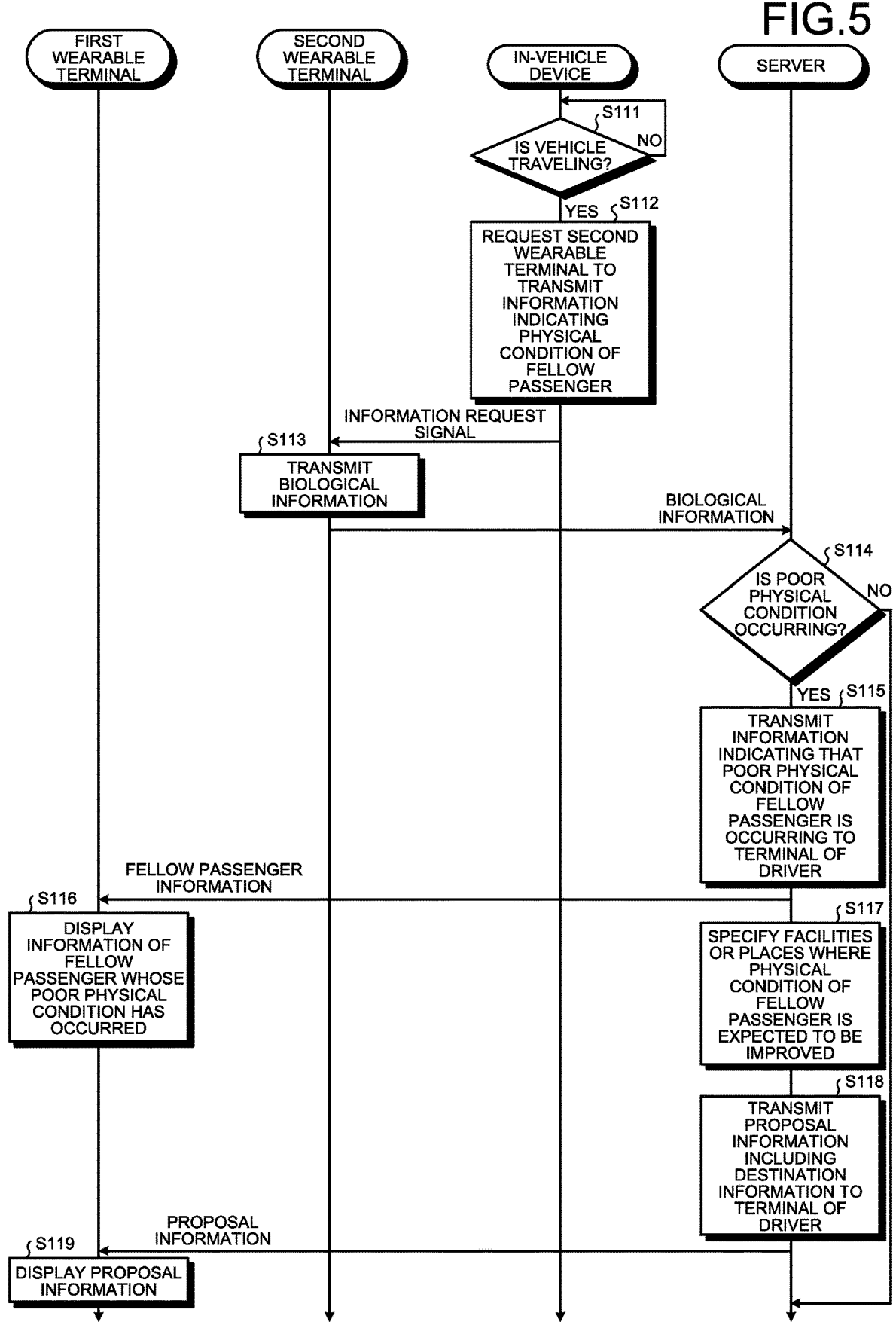
FIG. 5 is a sequence diagram illustrating control for providing information regarding a physical condition of a fellow passenger to the wearable terminal of the driver.

FIG. 5 is a sequence diagram illustrating control for providing information regarding a physical condition of a fellow passenger to the wearable terminal of the driver. The control illustrated in FIG. 5 is control executed by the information providing system 1 for a vehicle, and is repeatedly executed while the vehicle 2 is traveling. In addition, after the registration information is registered in the storage unit 34 by the processing of Step S104 illustrated in FIG. 4 described above, the control illustrated in FIG. 5 is executed.

As illustrated in FIG. 5, the in-vehicle device 30 determines whether the vehicle 2 is traveling (Step S111). In Step S111, it is determined whether the vehicle 2 is traveling on the basis of a signal input from the vehicle speed sensor to the control unit 33.

In a case where the vehicle 2 is not traveling (Step S111: No), this control routine returns to Step S111.

In a case where the vehicle 2 is traveling (Step S111: Yes), the in-vehicle device 30 requests the second wearable terminal 20 to transmit information indicating the physical condition of the fellow passenger (Step S112). In Step S112, an information request signal requesting the second wearable terminal 20 worn by the fellow passenger to measure and transmit the biological information of the fellow passenger is transmitted to the second wearable terminal 20. The in-vehicle device 30 can specify the terminal of the driver by the processing in Step S104 described above with respect to the plurality of wearable terminals 3 detected in the vehicle interior, and can thus specify a terminal other than the terminal of the driver as the terminal of the fellow passenger. Specifically, the in-vehicle device 30 receives the response signals from the plurality of wearable terminals 3 existing in the vehicle interior in the determination processing in Step S101 described above, and can thus specify the terminal identification information of the second wearable terminal 20 on the basis of the terminal identification information included in the response signals.

When the second wearable terminal 20 receives the information request signal from the in-vehicle device 30, the second wearable terminal 20 measures the biological information of the fellow passenger and transmits the measured biological information to the server 40 (Step S113). In Step S113, the biological information measured by the measurement unit 22 is transmitted from the second wearable terminal 20 to the server 40 in response to the reception of the information request signal by the communication unit 21.

Specifically, the measurement unit 22 of the second wearable terminal 20 measures at least any one of the pulse, the blood pressure, the respiration rate, the body temperature, the perspiration amount, the pulse width, and the sleep state as the biological information of the fellow passenger. For example, the measurement unit 22 measures the biological information of the fellow passenger with respect to four measurement targets such as the pulse, the blood pressure, the respiration rate, and the body temperature. In Step S113, the communication unit 21 transmits the biological information including these four measured values and the terminal identification information of the second wearable terminal 20 to the server 40. Then, the server 40 receives the biological information including the four measured values and the terminal identification information from the second wearable terminal 20. Note that the second wearable terminal 20 measures biological information of the fellow passenger regardless of whether the information request signal is received from the in-vehicle device 30.

When the server 40 receives the biological information transmitted from the second wearable terminal 20 in response to the information request signal, the server 40 determines whether the poor physical condition of the fellow passenger is occurring on the basis of the biological information (Step S114).

Specifically, in Step S114, the server 40 determines the information of the second wearable terminal 20 corresponds to the information of which vehicle 2, on the basis of the terminal identification information received from the second wearable terminal 20 together with the biological information. In this case, the control unit 43 collates the terminal identification information stored in the vehicle information table by the processing of step S105 described above with the terminal identification information received in Step S114 with reference to the vehicle information table of the storage unit 44. Then, in a case where the terminal identification information stored in the vehicle information table by the processing of Step S105 and the terminal identification information received in Step S114 coincide with each other, the control unit 43 specifies that the information received in Step S114 is information regarding the vehicle information stored in Step S105 described above.

Further, in Step S114, the server 40 determines whether the measured value included in the biological information acquired by the communication unit 41 is out of a range of a predetermined normal value. The range of the normal value is information stored in the storage unit 44 in advance.

This determination processing is performed for each of the measured values. That is, since a plurality of measured values may be included in the biological information acquired by the communication unit 41, the determination processing described above is performed by comparing the ranges of the normal values set for each of the measurement items with the corresponding measured values, in Step S114. That is, the ranges of the normal values for each of the measurement items of the biological information are stored in the storage unit 44.

For example, in a case where the four measured values of the pulse, the blood pressure, the respiration rate, and the body temperature are included in the biological information acquired by the communication unit 41, the determination unit 42 determines whether each measured value is out of the range of the normal value. That is, the determination unit 42 compares the range of the normal value of the pulse and the measured value of the pulse with each other, compares the range of the normal value of the blood pressure and the measured value of the blood pressure with each other, compares the range of the normal value of the respiration rate and the measured value of the respiration rate with each other, and compares the range of the normal value of the body temperature and the measured value of the body temperature with each other. In this case, the determination unit 42 can determine that the physical condition of the fellow passenger is poor in a case where it can be determined that at least any one of the plurality of measured values included in the biological information is an abnormal value without being limited to a case where all of the measured values are abnormal values. As an example, for the four measured values described above, in a case where it is determined that the pulse and the body temperature are within the normal ranges, but the blood pressure and the respiration rate are out of the ranges of the normal values to be abnormal values, the determination unit 42 can determine that the poor physical condition of the fellow passenger is occurring.

In addition, in a case where it is determined in Step S114 that the poor physical condition of the fellow passenger is occurring, the server 40 can specify a type of poor physical condition. In this case, the server 40 specifies the type of poor physical condition with reference to the physical condition management table on the basis of the measured value (measurement item) determined to be the abnormal value. As an example, a case where the physical condition management information has a record in which the type of poor physical condition is "car sickness" and the measurement items that become the abnormal values are the "blood pressure" and the "respiration rate" will be described. In this case, when it is determined in Step S114 that the measured value of the "blood pressure" and the measured value of the "respiration rate" are the abnormal values, the server 40 can specify physical condition management information indicating that the "car sickness" is the type of poor physical condition as the corresponding information. In other words, in a case where the biological information includes measured values of a plurality of measurement items, the type of poor physical condition can be identified by collating the measured values determined to be the abnormal values with a combination of the measurement items that become the abnormal values.

In a case where it is determined that the poor physical condition of the fellow passenger is not being occurred (Step S114: No), this control routine ends.

In a case where it is determined that the poor physical condition of the fellow passenger is occurring (Step S114: Yes), the server 40 transmits information indicating that the poor physical condition of the fellow passenger is occurring to the first wearable terminal 10 of the driver (Step S115).

In Step S115, the control unit 43 of the server 40 generates fellow passenger information including the information indicating that the poor physical condition of the fellow passenger is occurring. The fellow passenger information is information including information indicating that a physical condition of the fellow passenger is a predetermined state. In this embodiment, the predetermined state indicates that the poor physical condition is occurring. In addition, the physical condition management information can be included in the fellow passenger information.

The physical condition management information included in the fellow passenger information includes information indicating at least the type of poor physical condition among the respective fields described above. That is, the control unit 43 can provide the information on the type of poor physical condition specified in Step S114 to the first wearable terminal 10. At this time, the control unit 43 executes information provision control for transmitting the generated fellow passenger information to the first wearable terminal 10. That is, it is possible to transmit the physical condition management information included in the fellow passenger information to the first wearable terminal 10. Note that the first wearable terminal 10, which becomes an information transmission target in Step S115, is the first wearable terminal 10 of the driver specified on the basis of the vehicle information table in Step S105 described above.

When the first wearable terminal 10 receives the fellow passenger information from the server 40, the first wearable terminal 10 displays the fellow passenger information on the display unit 13 (Step S116). In Step S116, the information indicating that the poor physical condition of the fellow passenger is occurring and the physical condition management information including the type of poor physical condition are displayed as the fellow passenger information. The driver can recognize physical information of the fellow passenger by visually recognizing the fellow passenger information displayed on the display unit 13. Therefore, the driver can take action to eliminate the poor physical condition of the fellow passenger. For example, in a case where the fellow passenger information indicating that the type of poor physical condition is "car sickness" is displayed on the display unit 13, the driver can talk to the fellow passenger to confirm a subjective symptom or transfer a coping method.

In addition, the server 40 specifies destination information indicating facilities or places where the physical condition of the fellow passenger is expected to be improved, according to the type of poor physical condition (Step S117). Destination information indicating facilities or places where it is considered to be able to cope with the poor physical condition according to the type of poor physical condition are included in the physical condition management information. For example, the physical condition management table has a field of "destination information" in addition to the fields described above. As an example, in a case of a record in which the "car sickness" is stored in the field of the "type of poor physical condition", information of a "road shoulder", a "parking lot", and a "commercial facility" is stored in the field of the "destination information". In a case of a record in which the "abdominal pain" is stored in the field of the "type of poor physical condition" as another record, information of a "service area", a "commercial facility", and a "facility where a public toilet is installed" is stored in the field of the "destination information".

Then, the server 40 generates proposal information including the destination information, and transmits the proposal information to the first wearable terminal 10 of the driver (Step S118). The proposal information includes the destination information, required time information indicating a required time and a distance from a current vehicle position to a destination, and information indicating a coping method of coping with the poor physical condition. That is, the control unit 43 of the server 40 executes information provision control for transmitting the destination information to the first wearable terminal 10 and transmitting the required time information to the first wearable terminal 10. Note that the required time information only needs to include at least information regarding the required time, and does not need to include information regarding the distance.

Information indicating the current vehicle position can be acquired using a global positioning system (GPS), a navigation device, road-vehicle communication, or the like. For example, in a case where the in-vehicle device 30 includes a GPS receiver or a navigation device, position information indicating the current vehicle position is transmitted from the in-vehicle device 30 to the server 40, and the server 40 specifies the vehicle position by receiving the position information. In addition, the communication unit 31 performs road-vehicle communication with the surrounding infrastructure. In this case, the in-vehicle device 30 can acquire the information indicating the current vehicle position by the road-vehicle communication by the communication unit 31. Alternatively, in a case where the wearable terminal 3 is mounted with a GPS receiver, the wearable terminal 3 transmits position information indicating the current vehicle position to the server 40, and the server 40 can identify the vehicle position by receiving the position information.

In Step S113, the server 40 can specify position information of a facility or a place corresponding to the destination information for a position close to the current vehicle position using the position information indicating the current vehicle position and the destination information. That is, the server 40 can set the specified position information as the destination. In addition, the server 40 can calculate the required time or the distance from the current vehicle position to the destination and generate required time information including the calculated required time or distance. As an example, the server 40 can perform the setting of the destination, the calculation of the required time, and the calculation of the distance as described above using information acquired by a GPS mounted in the vehicle 2. In this case, the server 40 specifies destination information corresponding to a facility or a place existing at a position closest to the current vehicle position and generates required time information indicating a required distance and time for the destination information. Then, the server 40 provides the proposal information including the generated required time information to the first wearable terminal 10.

When the first wearable terminal 10 receives the proposal information from the server 40, the first wearable terminal 10 displays the proposal information on the display unit 13 (Step S119). In Step S119, an image indicating that there is a facility or a place corresponding to the destination information in front of a traveling direction of the vehicle 2 is displayed on the display unit 13. For example, in a case where a "road shoulder" or a "commercial facility" is displayed on the display unit 13 as the destination information, the driver can select various actions such as stopping the vehicle 2 that is traveling on a nearby road shoulder or dropping in the next convenience store. In addition, in a case where "breathe slowly" is displayed on the display unit 13 as the information indicating the coping method, the driver can transfer the coping method such as "breathe slowly" to the fellow passenger in the vehicle that is traveling.

Further, in a case where required time information indicating a required time and a distance from the current vehicle position to a facility or a place that becomes the destination is included in the proposal information received in Step S119, the required time information can be displayed on the display unit 13. At this time, since the vehicle 2 is traveling in the traveling direction, the server 40 updates the current vehicle position according to the traveling of the vehicle and recalculates the required time and the distance from the vehicle position to the destination to update the proposal information. The updated proposal information is transmitted from the server 40 to the first wearable terminal 10. Then, the first wearable terminal 10 can display the updated proposal information on the display unit 13. Therefore, the driver can grasp the required time and the like to the destination.

As described above, according to the embodiment, in a case where the poor physical condition of the fellow passenger has occurred while the vehicle 2 is traveling, the information regarding the physical condition of the fellow passenger can be provided to the driver using the wearable terminal 3 that can be worn by the occupant of the vehicle 2. Therefore, the driver can recognize that the physical condition of the fellow passenger has changed, by objective information, in a state where he/she continues to drive the vehicle.

For example, in the vehicle interior during the traveling of the vehicle, the driver recognizes that the poor physical condition of the fellow passenger has occurred and the physical condition of the fellow passenger, by self-report from the fellow passenger. For this reason, in a case where the fellow passenger underestimates deterioration of his/her physical condition and self-reports his/her physical condition, the driver recognizes that the physical condition of the fellow passenger is a slightly poor physical condition deviating from an actual physical condition. Alternatively, in a case where the fellow passenger endures deterioration of his/her physical condition and does not self-report his/her physical condition, the driver cannot recognize that the poor physical condition of the fellow passenger is occurring. According to the embodiment described above, the driver can recognize the physical condition of the fellow passenger while the vehicle is traveling, by objective information, regardless of subjectivity of the fellow passenger whose poor physical condition has occurred or subjectivity of the driver who becomes a recipient.

Note that a modification of the embodiment described above can be configured. For example, in the embodiment described above, in Steps S102 and S103 illustrated in FIG. 4, when the first wearable terminal 10 worn by the driver is specified, the first wearable terminal 10 transmits the registration information in response to the identification request signal from the in-vehicle device 30, but the present disclosure is not limited thereto. As a modification of the information providing system 1 for a vehicle, in Step S101, in a case where the detection unit 32 of the in-vehicle device 30 decides that a response signal transmitted from an area corresponding to the driver's seat 2a has been received, the detection unit 32 specifies that a terminal that has transmitted the response signal is the first wearable terminal 10 of the driver. For example, the communication unit 31 includes an antenna installed in the vehicle interior. The detection unit 32 specifies the terminal of the driver on the basis of a radio wave intensity of a signal received by the antenna of the communication unit 31. The antenna of the communication unit 31 is installed at a position closer to the driver's seat 2a than a passenger seat or the rear seat 2b, and a signal having the highest radio wave intensity among a plurality of response signals received by the antenna is determined, and the determined response signal is specified as a signal transmitted from the terminal of the driver. In this case, a signal transmitted from an area corresponding to the rear seat 2b is attenuated by a distance, an obstacle, or the like when being received by the antenna arranged in the vicinity the driver's seat 2a, and is thus received with a weak radio wave intensity. Alternatively, a plurality of such antennas may be arranged in the vehicle interior. For example, the antenna of the communication unit 31 includes a second antenna installed in the vicinity of the passenger seat or the rear seat 2b. In this case, a terminal that has transmitted a signal having the highest signal intensity among signals received by the second antenna is specified as the second wearable terminal 20 of the fellow passenger. Further, in Step S101, the detection unit 32 generates a detection signal indicating that the first wearable terminal 10 and the second wearable terminal 20 have been detected, and outputs the detection signal to the control unit 33. In this case, the processing of Steps S102 and S103 described above is omitted. Then, in Step S104, the control unit 33 registers the first wearable terminal 10 of the driver on the basis of the detection signal input from the detection unit 32.

In addition, a configuration in which the determination unit 42 of the server 40 performs the physical condition determination processing using the range of the normal value has been described in the embodiment described above, but the present disclosure is not limited thereto. As a modification of the information providing system 1 for a vehicle, the determination unit 42 monitors a fluctuation in the measured value included in the biological information and determines whether this fluctuation is a fluctuation exceeding a preset threshold value. In a case where this fluctuation is a fluctuation exceeding a predetermined threshold value, it is determined that the physical condition of the fellow passenger is rapidly changing. This fluctuation is a change amount in the measured value over time. That is, the determination unit 42 can determine the physical condition of the fellow passenger using a change amount in the measured value per predetermined time. The predetermined threshold value is stored in the storage unit 44 in advance. Therefore, it can be determined that the poor physical condition of the fellow passenger is occurring. In addition, even though a measurement result of the biological information is within the range of the normal value, it is possible to determine a sudden change in the physical condition that becomes an omen of the poor physical condition. Then, these determination results can be provided to the first wearable terminal 10 of the driver as information.

In addition, a case where the number of fellow passengers is one has been described in the embodiment described above, but the present disclosure is not limited thereto, and the number of fellow passengers may be plural. In a case where the number of fellow passengers is plural, a plurality of second wearable terminals 20 exist in the vehicle interior. The plurality of second wearable terminals 20 measure biological information of each fellow passenger and transmit the measured biological information to the server 40, respectively. In addition, the in-vehicle device 30 transmits vehicle information including all terminal identification information of the plurality of second wearable terminals 20 detected in the vehicle interior to the server 40. When the server 40 receives the biological information from each second wearable terminal 20 and the vehicle information from the in-vehicle device 30, the server 40 stores information included in the vehicle information in the vehicle information table and associates biological information regarding a plurality of fellow passengers who are in the same vehicle 2 with each other on the basis of the terminal identification information of the corresponding second wearable terminals 20. Corresponding records of the biological information table and the vehicle information table are associated with each other by the terminal identification information of the second wearable terminals 20. In addition, the server 40 determines whether a poor physical condition is occurring for the plurality of fellow passengers in the same vehicle. Then, in a case where the server 40 determines that the poor physical condition of at least one of the plurality of fellow passengers is occurring, the server 40 transmits fellow passenger information including information indicating that the poor physical condition of the fellow passenger is occurring to the first wearable terminal 10 in the same vehicle. At this time, in a case where it is determined that the poor physical conditions of the plurality of fellow passengers are simultaneously occurring, the server 40 transmits a plurality of fellow passenger information to the first wearable terminal 10, and the first wearable terminal 10 simultaneously displays the plurality of fellow passenger information on the display unit 13. Therefore, the driver can recognize that the poor physical conditions of the plurality of fellow passengers are occurring.

In addition, a configuration example in which the information is provided to the first wearable terminal 10 of the driver has been described in the embodiment described above, but the information may be provided to the second wearable terminal 20 of the fellow passenger. For example, in a case where the number of fellow passengers is plural, a total of four persons, that is, a father who is the driver, and a mother and two children who are the passengers, are in the vehicle 2. In this case, information based on biological information measured by second wearable terminals 20 worn by the children can be provided to a second wearable terminal 20 worn by the mother. As such, an information provision target is not limited to the first wearable terminal 10 of the driver, and may be the second wearable terminal 20 of another fellow passenger.

In addition, the wearable terminal 3 described above is an example, and the present disclosure is not limited thereto. For example, the first wearable terminal 10 worn by the driver may include a measurement unit having a function similar to that of the measurement unit 22 of the second wearable terminal 20. In addition, a type of second wearable terminal 20 worn by the fellow passenger is not particularly limited, and may be a wristband type, a watch type, a glasses type, a wearable type as an inner, or the like.

In addition, data structures of the various tables described above are examples, and the present disclosure is not limited thereto. For example, in the physical condition management table, the fields of the "type of poor physical condition" and the "measurement item that becomes an abnormal value" are essential, but the other fields are not limited to the example described above. That is, the physical condition management table only needs to have at least the fields of the "type of poor physical condition" and the "measurement item that becomes an abnormal value", and does not need to have the field of the "symptom" described above. Alternatively, another field that is not described above may be added to the physical condition management table.

Further, the information stored in each field of the various tables described above is not limited to the embodiment described above. For example, in the physical condition management table, the information stored in the "measurement item that becomes an abnormal value" is not limited to the example described above. As a modification of the physical condition management table, in a record in which the "abdominal pain" is the "type of poor physical condition", the information stored in the field of the "measurement item that becomes an abnormal value" may be information other than a combination of the "pulse", the "body temperature", and the "respiration rate". In addition, only a case where the plurality of information is stored in the field of the "measurement item that becomes an abnormal value" has been described in the embodiment described above, but the present disclosure is not limited thereto. That is, only one information such as only a "pulse" may be stored in the field of the "measurement item that becomes an abnormal value". In addition, the same information may be stored in the field of the "type of poor physical condition" and the field of the "symptom". For example, in a record in which the "abdominal pain" is stored in the field of the "type of poor physical condition", the "abdominal pain" may be stored in the field of the "symptom".

In addition, a method of specifying the type of poor physical condition is not limited to the method by a combination of the measurement items that become abnormal values described above. In short, in a case where the server 40 determines that the measured value is the abnormal value on the basis of the measured value included in the biological information, the server 40 can specify the type of poor physical condition on the basis of the measured value determined to be the abnormal value. That is, information referred to at the time of specifying the type of poor physical condition is not limited to the physical condition management information described above, and may be, for example, another information stored in another database.

In addition, a case where a poor physical condition of a fellow passenger whose physical condition was good occurs while the vehicle is traveling has been described in the embodiment described above, but the present disclosure is not limited thereto. For example, the information providing system 1 for a vehicle can be applied to a case where a fellow passenger who has already been in a bad physical condition before getting in the vehicle 2 gets in the vehicle 2 and the vehicle 2 then travels, or the like. Further, the information providing system 1 for a vehicle can inform the driver of the physical condition but also fellow passenger information including information indicating that the physical condition of the fellow passenger has changed. Control of this modification is illustrated in FIGS. 6 to 9.

Figure 6:
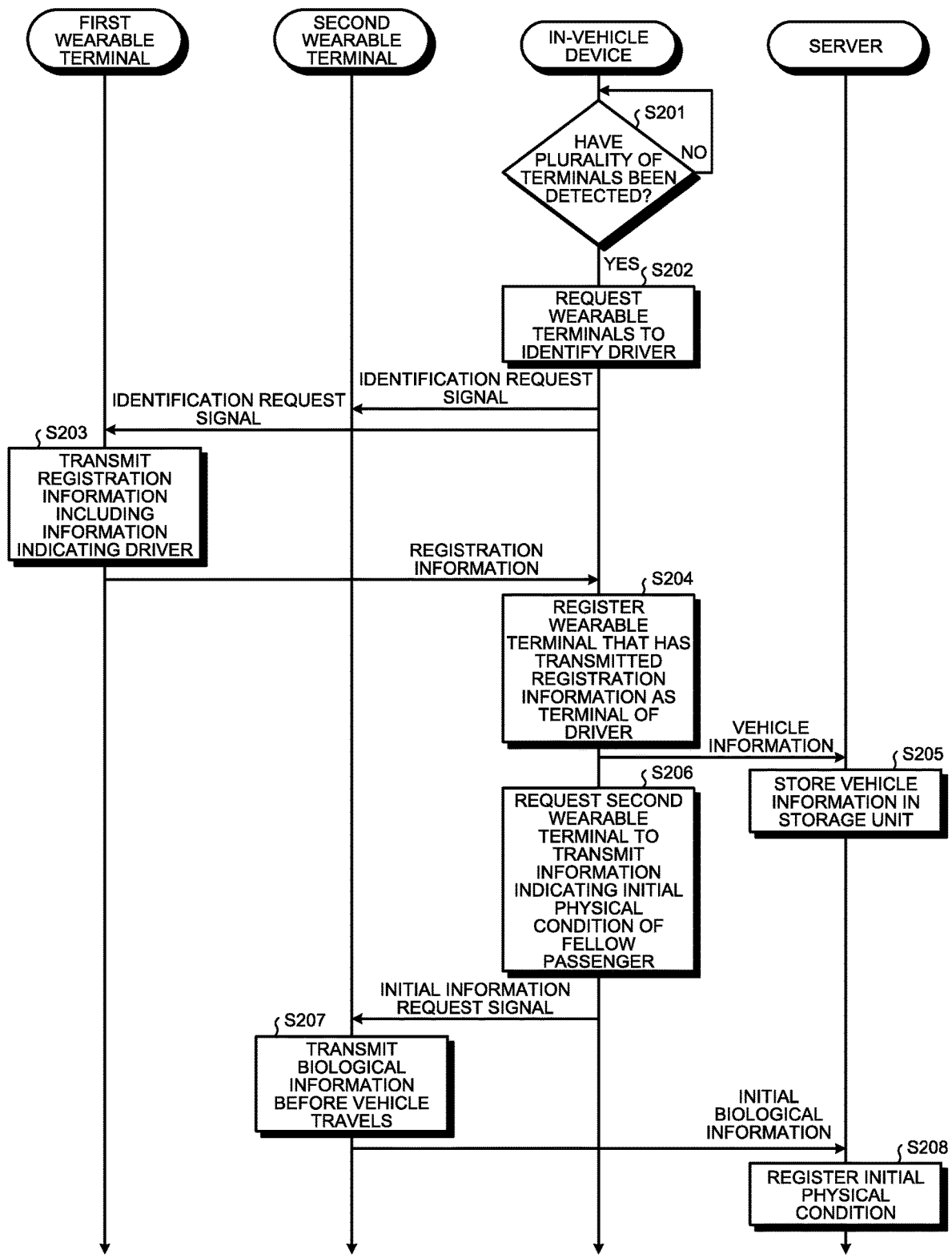
FIG. 6 is a sequence diagram illustrating control for registering an initial physical condition of a fellow passenger as a modification.
Figure 7:
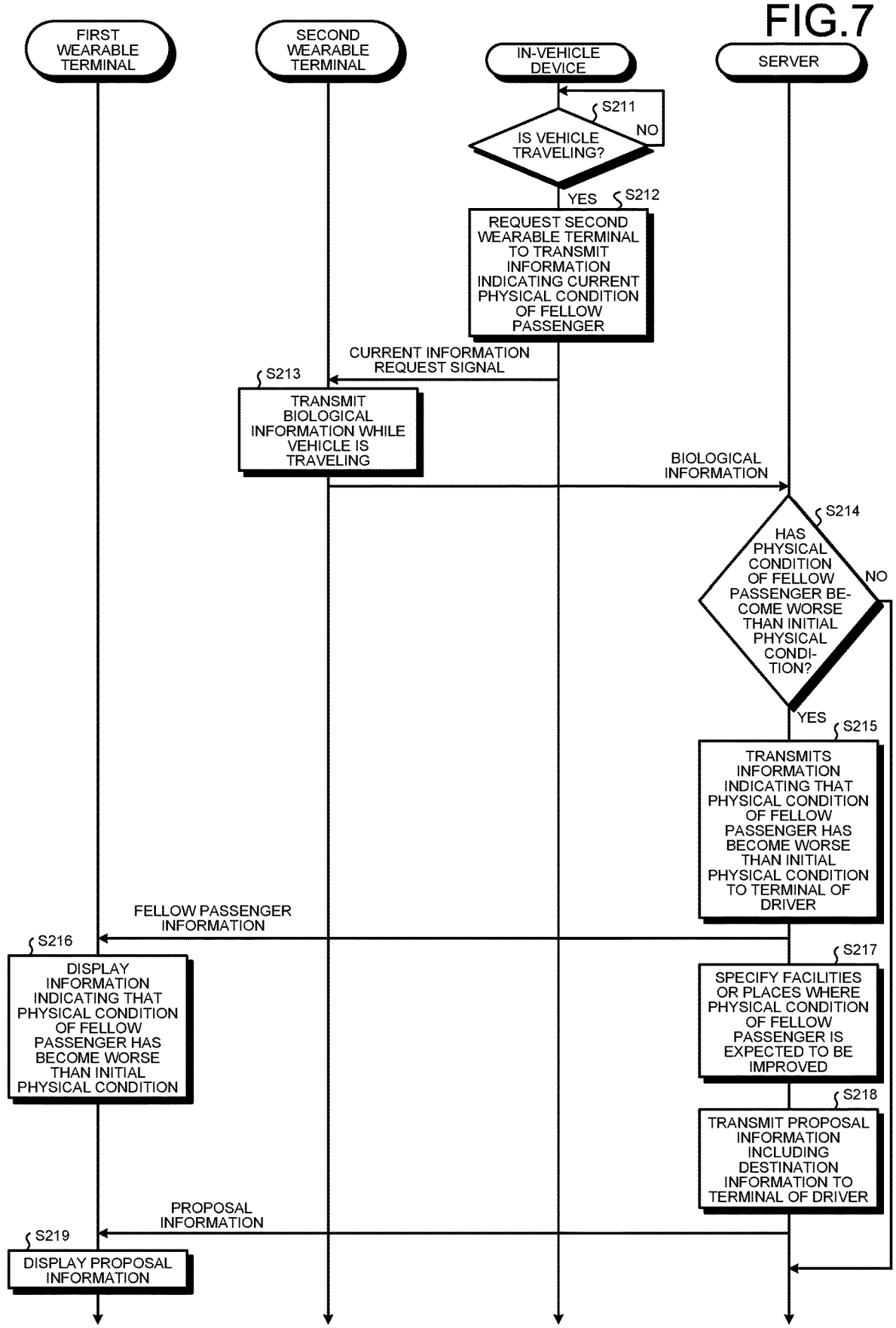
FIG. 7 is a sequence diagram illustrating control for providing information indicating a change in the physical condition of the fellow passenger to the wearable terminal of the driver, as a modification.

First, an example of a modification will be described with reference to FIGS. 6 and 7. Control illustrated in FIG. 6 is a modification of the control illustrated in FIG. 4. Control illustrated in FIG. 7 is a modification of the control illustrated in FIG. 5.

FIG. 6 is a sequence diagram illustrating control for registering an initial physical condition of a fellow passenger as a modification. Note that Steps S201 to S205 illustrated in FIG. 6 are the same processing as that of Steps S101 to S105 illustrated in FIG. 4, and a description thereof will thus be omitted.

As illustrated in FIG. 6, when the in-vehicle device 30 registers the first wearable terminal 10 of the driver in Step S204, the in-vehicle device 30 requests the second wearable terminal 20 to transmit information (initial information) indicating an initial physical condition of the fellow passenger (Step S206). In Step S206, in a state in which the vehicle 2 is being stopped, an initial information request signal requesting the second wearable terminal 20 worn by the fellow passenger to measure and transmit the biological information of the fellow passenger is transmitted to the second wearable terminal 20.

When the second wearable terminal 20 receives the initial information request signal from the in-vehicle device 30, the second wearable terminal 20 measures biological information of the fellow passenger before the vehicle travels, and transmits the measured biological information (initial biological information) to the server 40 (Step S207). In Step S207, the biological information measured by the measurement unit 22 is transmitted from the second wearable terminal 20 to the server 40 in response to the reception of the initial information request signal by the communication unit 21.

When the server 40 receives the initial biological information from the second wearable terminal 20, the server 40 registers the initial biological information as the initial physical condition (Step S208). The storage unit 44 stores the initial biological information in the biological information table.

FIG. 7 is a sequence diagram illustrating control for providing information indicating a change in the physical condition of the fellow passenger to the wearable terminal of the driver, as a modification. Note that Steps S211 and S217 to S219 illustrated in FIG. 7 are the same processing as that of Steps S111 and S117 to S119 illustrated in FIG. 5, and a description thereof will thus be omitted.

As illustrated in FIG. 7, in a case where the vehicle 2 is traveling (Step S211: Yes), the in-vehicle device 30 requests the second wearable terminal 20 to transmit information (current information) indicating a current physical condition of the fellow passenger (Step S212). In Step S212, in a state in which the vehicle 2 is traveling, a current information request signal requesting the second wearable terminal 20 worn by the fellow passenger to measure and transmit the biological information of the fellow passenger is transmitted to the second wearable terminal 20.

When the second wearable terminal 20 receives the current information request signal from the in-vehicle device 30, the second wearable terminal 20 measures biological information of the fellow passenger while the vehicle is traveling, and transmits the measured biological information to the server 40 (Step S213). In Step S213, the biological information measured by the measurement unit 22 is transmitted from the second wearable terminal 20 to the server 40 in response to the reception of the current information request signal by the communication unit 21.

When the server 40 receives the biological information transmitted from the second wearable terminal 20 in response to the current information request signal, the server 40 determines whether the physical condition of the fellow passenger has become worse than the initial physical condition by comparing this biological information and the initial biological information with each other (Step S214). In Step S214, in a case where it is detected that a measured value that was within the range of the normal value in the initial biological information is out of the range of the normal value in current biological information, it is determined that the physical condition of the fellow passenger has become worse. In addition, in Step S214, in a case where it is determined that a measured value is within the range of the normal value in both of the initial biological information and the current biological information, but a current measured value becomes closer to the abnormal value than an initial measured value is, it is determined that the physical condition of the fellow passenger has become worse. Further, in Step S214, in a case where an abnormal value is originally included in the initial biological information, when it is determined that a degree at which a measured value determined to be the abnormal value deviates from the range of the normal value becomes larger in the current biological information than in the initial biological information, it is determined that the physical condition of the fellow passenger has become worse. This deviation degree is a preset value, is stored in the storage unit 44, and is set for each measurement item.

When it is determined that the physical condition of the fellow passenger has not become worse from the initial physical condition (Step S214: No), this control routine ends.

In a case where it is determined that the physical condition of the fellow passenger has become worse than the initial physical condition (Step S214: Yes), the server 40 transmits information indicating that the physical condition of the fellow passenger has become worse than the initial physical condition to the first wearable terminal 10 of the driver (Step S215). In Step S215, the control unit 43 of the server 40 generates fellow passenger information including information indicating that the physical condition of the fellow passenger has become worse than the initial physical condition. This fellow passenger information is provided to the first wearable terminal 10.

When the first wearable terminal 10 receives the fellow passenger information from the server 40, the first wearable terminal 10 displays the fellow passenger information on the display unit 13 (Step S216). In Step S216, the information indicating that the physical condition of the fellow passenger has become worse than the initial physical condition is displayed as the fellow passenger information.

Figure 8:
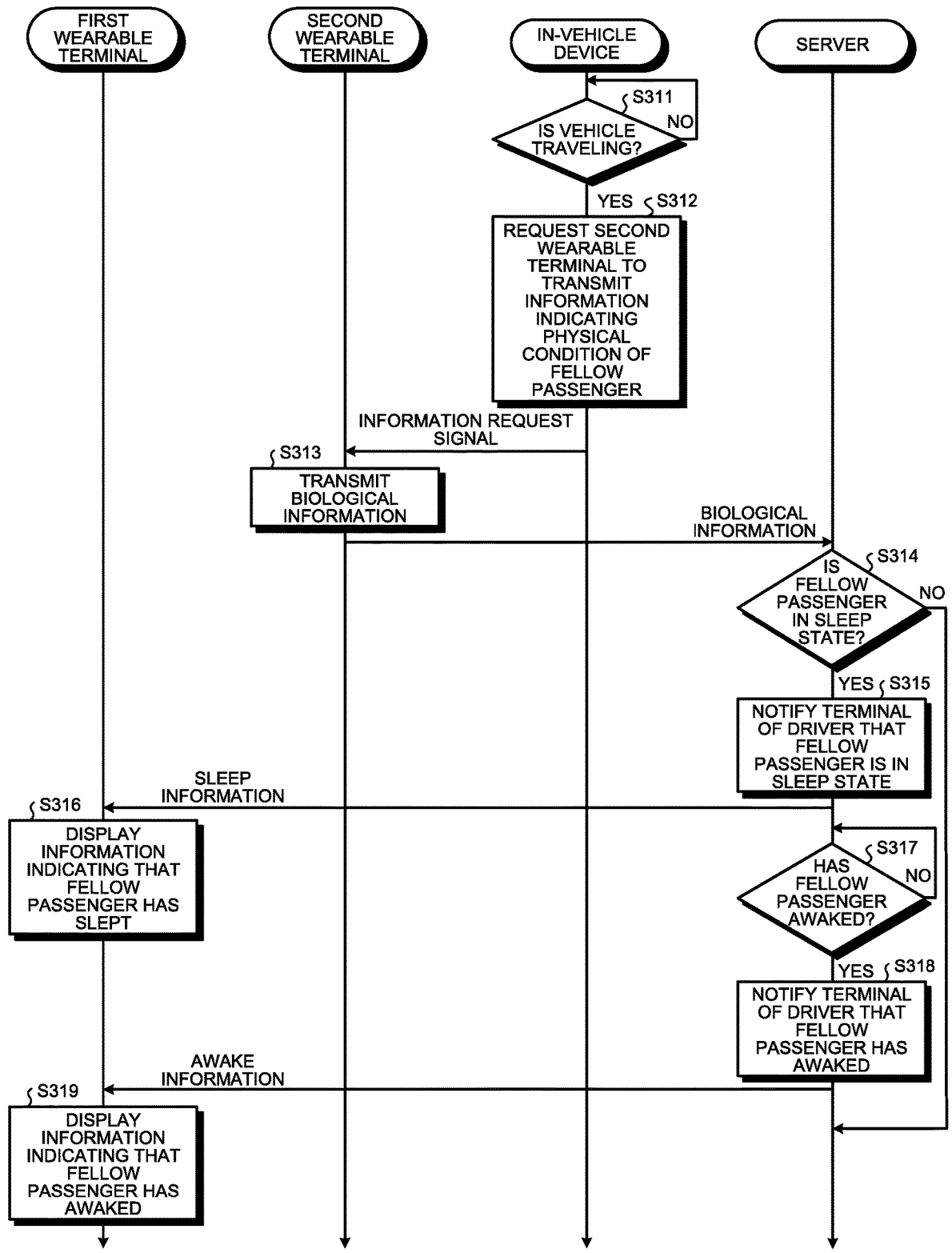
FIG. 8 is a sequence diagram illustrating control for providing information indicating that the fellow passenger is in a sleep state to the wearable terminal of the driver, as another modification.

Next, another modification will be described with reference to FIG. 8. Control illustrated in FIG. 8 is a modification of the control illustrated in FIG. 5. Therefore, the control illustrated in FIG. 8 may be performed after the control illustrated in FIG. 4 described above is performed.

FIG. 8 is a sequence diagram illustrating control for providing information indicating that the fellow passenger is in a sleep state to the wearable terminal of the driver, as another modification. Note that Steps S311 to S313 illustrated in FIG. 8 are the same processing as that of Steps S111 to S113 illustrated in FIG. 5, and a description thereof will thus be omitted. In addition, the determination unit 42 according to this modification determines whether the fellow passenger is in a sleep state as a predetermined state.

As illustrated in FIG. 8, when the server 40 receives the biological information transmitted from the second wearable terminal 20 in response to the information request signal, the server 40 determines whether the fellow passenger is in the sleep state on the basis of the biological information (Step S314). In Step S314, it is determined whether the physical condition of the fellow passenger has transitioned from an awake state to the sleep state on the basis of a measured value of the sleep state included in the biological information.

In a case where it is determined that the fellow passenger is not in the sleep state (Step S314: No), this control routine ends.

In a case where it is determined that the fellow passenger is in the sleep state (Step S314: Yes), the server 40 transmits sleep information indicating that the fellow passenger is in the sleep state to the first wearable terminal 10 of the driver (Step S315). In Step S315, the control unit 43 of the server 40 can generate fellow passenger information including the information indicating that the fellow passenger is in the sleep state, and transmit the fellow passenger information to the first wearable terminal 10.

When the first wearable terminal 10 receives the sleep information from the server 40, the first wearable terminal 10 displays the sleep information on the display unit 13 (Step S316). In Step S316, the sleep information indicating that the fellow passenger is in the sleep state is displayed as fellow passenger information. For example, in a case where the fellow passenger is a child and the driver is a parent, the driver may drive the vehicle while paying attention to whether the child is sleeping. As an example, when the vehicle 2 travels a long distance at midnight, the parent who is the driver can continue driving while recognizing that the child who is the fellow passenger is in the sleep state. In addition, it is also applicable to a case where the fellow passenger is a child sitting on a child seat.

Further, the server 40 determines whether the fellow passenger has awaked on the basis of the biological information of the second wearable terminal 20 (Step S317). In Step S317, it is determined whether the physical condition of the fellow passenger has transitioned from the sleep state to the awake state on the basis of the measured value of the sleep state included in the biological information.

In a case where it is not determined that the fellow passenger has awaked (Step S317: No), this control routine repeats the determination processing of Step S317.

In a case where it is determined that the fellow passenger has awaked (Step S317: Yes), the server 40 transmits awake information indicating that the fellow passenger has awaked to the first wearable terminal 10 of the driver (Step S318). In Step S318, the control unit 43 of the server 40 can generate fellow passenger information including the awake information indicating that the fellow passenger has awaked, and transmit the fellow passenger information to the first wearable terminal 10.

When the first wearable terminal 10 receives the awake information from the server 40, the first wearable terminal 10 displays the awake information on the display unit 13 (Step S319). In Step S319, the awake information indicating that the fellow passenger has awaked is displayed as fellow passenger information. For example, in a case where the fellow passenger is a child and the driver is a parent, the driver may drive the vehicle while paying attention to whether the child who was sleeping has awaked. As an example, when the vehicle 2 travels a long distance at midnight, the parent who is the driver can recognize that the child who is the fellow passenger has awaked from the sleep state. Therefore, the driver can confirm an intention of the fellow passenger about whether the fellow passenger would like to rest to go to a toilet.

Figure 9:
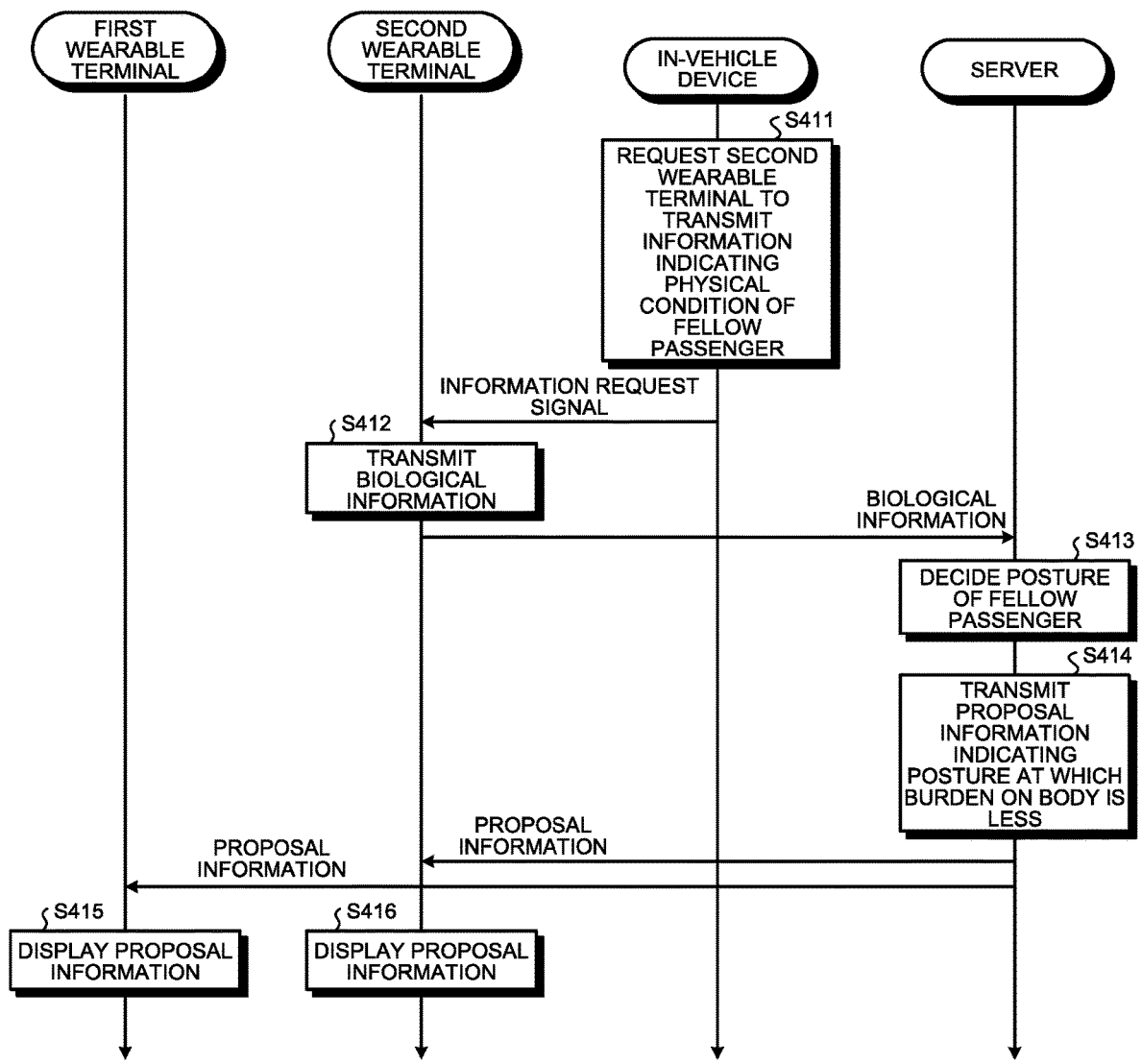
FIG. 9 is a sequence diagram illustrating control for providing information regarding a posture of the fellow passenger to the wearable terminal of the driver, as still another modification.

Next, still another modification will be described with reference to FIG. 9. Control illustrated in FIG. 9 is performed by the information providing system 1 for a vehicle after the control illustrated in FIG. 4 described above is performed. In addition, the control illustrated in FIG. 9 can be said to be a modification of the control illustrated in FIG. 7 described above because it is assumed that a poor physical condition of the fellow passenger has already occurred before the fellow passenger gets in the vehicle.

FIG. 9 is a sequence diagram illustrating control for providing information regarding a posture of the fellow passenger to the wearable terminal of the driver, as still another modification.

As illustrated in FIG. 9, when the in-vehicle device 30 registers the first wearable terminal 10 of the driver in Step S404, the in-vehicle device 30 requests the second wearable terminal 20 to transmit information indicating a physical condition of the fellow passenger (Step S411). In Step S411, in a state in which the vehicle 2 is being stopped, an information request signal requesting the second wearable terminal 20 worn by the fellow passenger to measure and transmit the biological information of the fellow passenger is transmitted to the second wearable terminal 20.

When the second wearable terminal 20 receives the information request signal from the in-vehicle device 30, the second wearable terminal 20 measures biological information of the fellow passenger before the vehicle travels, and transmits the measured biological information to the server 40 (Step S412). In Step S412, the biological information including a measured value measured by the acceleration sensor in the measurement unit 22 is transmitted from the second wearable terminal 20 to the server 40.

When the server 40 receives the biological information from the second wearable terminal 20, the server 40 decides a posture of the fellow passenger on the basis of the physical condition (Step S413). In Step S413, the posture of the fellow passenger is decided by the server 40 on the basis of the measured value of the acceleration sensor, included in the biological information. In this case, the server 40 can determine whether the posture is a posture at which a burden on the fellow passenger is heavy, on the basis of another measured value included in the biological information, for example, a respiration rate or a pulse.

Then, the server 40 generates proposal information indicating a posture at which a burden on the body is less, and transmits the proposal information to the first wearable terminal 10 and the second wearable terminal 20 (Step S414). For example, the server 40 determines the posture on the basis of the respiration rate included in the biological information, and proposes a posture determined to be easier to breathe than a posture determined to be difficult to breathe, as the proposal information.

When the first wearable terminal 10 receives the proposal information from the server 40, the first wearable terminal 10 displays the proposal information on the display unit 13 (Step S415). Similarly, when the second wearable terminal 20 receives the proposal information from the server 40, the second wearable terminal 20 displays the proposal information on the display unit 24 (Step S416). As such, by providing the proposal information to both of the terminal worn by the driver and the terminal worn by the fellow passenger, the fellow passenger can be aware of how to change his/her posture in order to reduce his/her burden, and it becomes possible to support the driver to improve the posture of the passenger by sharing the recognition with the passenger.

As such, it is possible to configure the information providing system 1 for a vehicle so that the control illustrated in FIGS. 6 to 9 can be executed.

In addition, a system configuration in which the server 40 includes one server has been described in the embodiment or the various modifications described above, but the present disclosure is not limited thereto. The server 40 can be divided into a plurality of servers. That is, the functions included in the server 40 described above can be configured to be divided into the plurality of servers to cause the plurality of servers to cooperate with each other.

In addition, a system configuration in which the in-vehicle device 30 and the server 40 are provided as the information providing device has been described in the embodiment or the various modifications described above, but the present disclosure is not limited thereto. In short, the information providing device is not limited to a configuration including both of the in-vehicle device 30 and the server 40, and may include, for example, only the in-vehicle device 30. In this modification, the functions of the server 40 described above can be integrated into the in-vehicle device 30. That is, as a modification, the in-vehicle device 30 can include the functions of the communication unit 41, the determination unit 42, the control unit 43, and the storage unit 44 of the server 40 described above.

In addition, in the first wearable terminal 10 described above, the output of the voice information by the speaker 16 has been described, but the output (voice guidance) of the voice information is not limited to the output from the speaker 16, and may be an output method using bone conduction. Since the first wearable terminal 10 includes a contact portion in contact with the head of the driver, it is possible to provide the voice guide to the driver by bone conduction from this contact portion. Further, a storage place of the voice information is not limited to the storage unit 14 of the first wearable terminal 10, but may be the storage unit 44 of the server 40 or the storage unit 34 of the in-vehicle device 30.

According to the present disclosure, while the vehicle is traveling, the biological information of the fellow passenger is measured by the second mobile terminal worn by the fellow passenger and the information providing device determines the physical condition of the fellow passenger on the basis of the measured biological information. Then, the information providing device provides the information regarding the physical condition of the fellow passenger by an objective determination result to the first mobile terminal that can be worn by the driver. Therefore, the driver can recognize the physical condition of the fellow passenger while the vehicle is traveling.

According to an embodiment, the information providing device can determine whether the poor physical condition of the fellow passenger is occurring on the basis of at least any one of the pulse, the blood pressure, the respiration rate, the body temperature, the perspiration amount, and the pulse width. Then, a result of the determination is displayed on the display unit of the first mobile terminal worn by the driver. Therefore, the driver can recognize that the poor physical condition of the fellow passenger is occurring while the vehicle is traveling by visually recognizing the information displayed on the display unit.

According to an embodiment, the information providing device can determine whether the measured value is the abnormal value by comparing the measured value of the biological information with the range of the normal value. In addition, the information providing device specifies the type of poor physical condition on the basis of the measured value determined to be the abnormal value and transmits information indicating the specified type of poor physical condition to the first mobile terminal, and the first mobile terminal displays the information indicating the type of poor physical condition on the display unit. Therefore, the driver can recognize the type of poor physical condition by visually recognizing the information displayed on the display unit.

According to an embodiment, the information indicating the type of poor physical condition and the information indicating the coping method of coping with the poor physical condition are displayed on the display unit of the first mobile terminal. Therefore, the driver can recognize the coping method of coping with the poor physical condition by visually recognizing the information displayed on the display unit.

According to an embodiment, the destination information indicating the facility or the place where the physical condition of the fellow passenger is expected to be improved according to the type of poor physical condition is displayed on the display unit of the first mobile terminal. Therefore, the driver can examine a destination of the vehicle for improving the physical condition by visually recognizing the destination information displayed on the display unit.

According to an embodiment, the required time information indicating the required time from the facility or the place which becomes the destination is displayed on the display unit of the first mobile terminal. Therefore, the driver can recognize how long it takes to arrive at the destination by visually recognizing the required time information displayed on the display unit.

According to an embodiment, the required time information displayed on the display unit of the first mobile terminal is updated as the vehicle travels. Therefore, the driver can more accurately recognize how long it takes to arrive at the destination by visually recognizing the required time information displayed on the display unit.

According to an embodiment, the information providing device can determine whether the fellow passenger is in the sleep state and transmit the sleep information to the first mobile terminal according to a result of the determination. Therefore, the driver can recognize that the fellow passenger is in the sleep state in a vehicle interior while the vehicle is traveling, on the basis of the sleep information displayed by the display unit.

According to an embodiment, it is possible to determine whether the physical condition of the fellow passenger is the predetermined state by the in-vehicle device, and it is possible to provide information to the first mobile terminal of the driver according to a result of the determination. Therefore, it becomes unnecessary to perform communication with the outside of the vehicle via a network. For this reason, even in a situation where the vehicle is traveling in an environment where the in-vehicle device cannot communicate with the outside, it becomes possible to transmit information regarding the physical condition of the fellow passenger to the first mobile terminal of the driver.

According to an embodiment, it is possible to determine whether the physical condition of the fellow passenger is the predetermined state by the server, and it is possible to provide information to the first mobile terminal of the driver through a network according to a result of the determination. Therefore, while the vehicle is traveling, the driver can recognize the physical condition of the fellow passenger by the information provided from the first mobile terminal.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An information providing system for a vehicle, comprising:
    a first mobile terminal that is worn by a driver of the vehicle;
    a second mobile terminal that is worn by a fellow passenger of the vehicle; and
    an information providing device that transmits and receives information to and from the first mobile terminal and the second mobile terminal,
    wherein the first mobile terminal includes:
    a first communication unit that transmits and receives information to and from the information providing device; and
    a display unit that displays the information received by the first communication unit within a field of view of the driver in a state where the first mobile terminal is worn by the driver,
    the second mobile terminal includes:
    a measurement unit that measures biological information of the fellow passenger in a state where the second mobile terminal is worn by the fellow passenger while the vehicle is traveling; and
    a second communication unit that transmits the biological information measured by the measurement unit to the information providing device, and
    the information providing device includes:
    a third communication unit that receives the biological information transmitted from the second mobile terminal and transmits information to the first mobile terminal, while the vehicle is traveling;
    a determination unit that determines whether a physical condition of the fellow passenger is a predetermined state on the basis of the biological information received by the third communication unit; and
    a control unit that executes information provision control for generating information indicating that the physical condition of the fellow passenger is the predetermined state and transmitting the generated information to the first mobile terminal, in a case where it is determined by the determination unit that the physical condition of the fellow passenger is the predetermined state.

2. The information providing system for a vehicle according to claim 1, wherein the predetermined state is a state where a poor physical condition of the fellow passenger is occurring,
    the biological information includes at least any one of a pulse, a blood pressure, a respiration rate, a body temperature, a perspiration amount, and a pulse width,
    the determination unit determines whether the poor physical condition of the fellow passenger is occurring while the vehicle is traveling, on the basis of a measured value included in the biological information, and
    the control unit executes information provision control for transmitting information indicating that the poor physical condition of the fellow passenger is occurring to the first mobile terminal in a case where it is determined by the determination unit that the poor physical condition of the fellow passenger is occurring.

3. The information providing system for a vehicle according to claim 2, wherein the determination unit
    determines whether the measured value is an abnormal value which is out of a range of a predetermined normal value and
    determines that the poor physical condition of the fellow passenger is occurring in the case where the measured value is determined to be the abnormal value, and
    the control unit executes information provision control for specifying a type of poor physical condition on the basis of the measured value determined to be the abnormal value and transmitting the specified information indicating the type of poor physical condition to the first mobile terminal, in the case where it is determined by the determination unit that the poor physical condition of the fellow passenger is occurring.

4. The information providing system for a vehicle according to claim 3, wherein the control unit executes information provision control for transmitting information indicating a coping method of coping with the poor physical condition to the first mobile terminal, together with the information indicating the type of poor physical condition, when transmitting the information indicating the type of poor physical condition to the first mobile terminal.

5. The information providing system for a vehicle according to claim 3, wherein the control unit executes information provision control for transmitting destination information indicating a facility or a place where the physical condition of the fellow passenger is expected to be improved according to the type of poor physical condition to the first mobile terminal, together with the information indicating the type of poor physical condition, when transmitting the information indicating the type of poor physical condition to the first mobile terminal.

6. The information providing system for a vehicle according to claim 5, wherein the control unit executes control for generating required time information indicating a required time from a current vehicle position to the facility or the place on the basis of a relative position relationship between first position information indicating a position of the facility or the place corresponding to the destination information and second position information indicating the current vehicle position, when transmitting the destination information to the first mobile terminal, and executes information provision control for transmitting the generated required time information to the first mobile terminal together with the destination information.

7. The information providing system for a vehicle according to claim 6, wherein the control unit executes control for updating the required time information on the basis of a transition of the second position information and executes information provision control for transmitting the updated required time information to the first mobile terminal, when the second position information indicating the current vehicle position is updated according to the traveling of the vehicle.

8. The information providing system for a vehicle according to claim 1, wherein the predetermined state includes a sleep state, the determination unit determines whether the fellow passenger is in the sleep state on the basis of the biological information, and the control unit executes information provision control for transmitting sleep information indicating that the fellow passenger is in the sleep state to the first mobile terminal in a case where it is determined by the determination unit that the fellow passenger is in the sleep state.

9. The information providing system for a vehicle according to claim 1, wherein the information providing device is an in-vehicle device that is mounted in the vehicle and controls the vehicle.

10. The information providing system for a vehicle according to claim 1, wherein the information providing device includes:

an in-vehicle device that is mounted in the vehicle and transmits and receives information to and from the first mobile terminal and the second mobile terminal; and a server that is installed outside the vehicle and transmits and receives information to and from the first mobile terminal, the second mobile terminal, and the in-vehicle device, the in-vehicle device including:

a detection unit that detects that the first mobile terminal and the second mobile terminal exist in a vehicle interior of the vehicle;

a vehicle-side control unit that executes communication control for generating vehicle information including each identification information of the first mobile terminal and the second mobile terminal detected by the detection unit and identification information of the vehicle and transmitting the vehicle information to the server; and a fourth communication unit that transmits the vehicle information to the server, the server including:

the third communication unit;

the determination unit; and the control unit, the first communication unit transmitting and receiving information to and from the server, the second communication unit transmitting terminal information including the biological information and the identification information of the second mobile terminal to the server, the third communication unit receiving the vehicle information transmitted from the in-vehicle device and receiving the terminal information transmitted from the second mobile terminal, the control unit executing control for specifying the first mobile terminal and the second mobile terminal existing in the vehicle interior of the vehicle and associating information regarding the specified vehicle, the first mobile terminal, and the second mobile terminal with each other, on the basis of the vehicle information and the terminal information received by the third communication unit, and executing the information provision control on the information regarding the vehicle, the first mobile terminal, and the second mobile terminal associated with each other, and the determination unit executing determination processing on the information regarding the vehicle, the first mobile terminal, and the second mobile terminal associated with each other by the control unit.

11. An information providing method for a vehicle executed by an information providing system for a vehicle, the information providing system for a vehicle including a first mobile terminal that is worn by a driver of the vehicle, a second mobile terminal that is worn by a fellow passenger of the vehicle, and an information providing device that transmits and receives information to and from the first mobile terminal and the second mobile terminal, the information providing method for a vehicle comprising:

a measuring step of measuring biological information of the fellow passenger by the second mobile terminal worn by the fellow passenger while the vehicle is traveling;

a first transmitting step of transmitting the measured biological information to the information providing device by the second mobile terminal;

a first receiving step of receiving the biological information transmitted from the second mobile terminal by the information providing device while the vehicle is traveling;

a determining step of determining whether a physical condition of the fellow passenger is a predetermined state on the basis of the received biological information, by the information providing device;

a generating step of generating information indicating that the physical condition of the fellow passenger is the predetermined state by the information providing device in a case where the physical condition of the fellow passenger is determined to be the predetermined state;

an information providing step of transmitting the generated information from the information providing device to the first mobile terminal;

a second receiving step of receiving the information provided from the information providing device by the first mobile terminal; and a displaying step of displaying the information received by the second receiving step within a field of view of the driver by the first mobile terminal worn by the driver.

12. An information providing device that transmits and receives information from and to a first mobile terminal worn a driver of a vehicle and a second mobile terminal worn by a fellow passenger of the vehicle, the information providing device comprising:

a communication unit that receives biological information of the fellow passenger measured and transmitted by the second mobile terminal worn by the fellow passenger while the vehicle is traveling;

a determination unit that determines whether a physical condition of the fellow passenger is a predetermined state on the basis of the received biological information; and a control unit that executes information provision control for generating information indicating that the physical condition of the fellow passenger is the predetermined state and transmitting the generated information to the first mobile terminal, in a case where it is determined that the physical condition of the fellow passenger is the predetermined state.

\* \* \* \* \*